(12) United States Patent
Hakonarson et al.

(10) Patent No.: US 12,091,708 B2
(45) Date of Patent: Sep. 17, 2024

(54) COMPOSITIONS AND METHODS TARGETING THE TH2 PATHWAY FOR THE TREATMENT OF ASTHMA

(71) Applicant: THE CHILDREN'S HOSPITAL OF PHILADELPHIA, Philadelphia, PA (US)

(72) Inventors: Hakon Hakonarson, Malvern, PA (US); Patrick Sleiman, Philadelphia, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 351 days.

(21) Appl. No.: 16/476,703

(22) PCT Filed: Jan. 9, 2018

(86) PCT No.: PCT/US2018/012963
§ 371 (c)(1),
(2) Date: Jul. 9, 2019

(87) PCT Pub. No.: WO2018/129529
PCT Pub. Date: Jul. 12, 2018

(65) Prior Publication Data
US 2019/0376127 A1    Dec. 12, 2019

Related U.S. Application Data

(60) Provisional application No. 62/607,269, filed on Dec. 18, 2017, provisional application No. 62/444,255, filed on Jan. 9, 2017.

(51) Int. Cl.
*C12Q 1/6883* (2018.01)
*C12Q 1/6827* (2018.01)

(52) U.S. Cl.
CPC ......... *C12Q 1/6827* (2013.01); *C12Q 1/6883* (2013.01); *C12Q 2600/106* (2013.01); *C12Q 2600/156* (2013.01)

(58) Field of Classification Search
CPC ............ C12Q 1/6883; C12Q 2600/106; C12Q 2600/156; C12Q 2600/172
See application file for complete search history.

(56) References Cited

U.S. PATENT DOCUMENTS

2011/0200583 A1    8/2011  Hakonarson et al.

FOREIGN PATENT DOCUMENTS

WO     2016/193151 A1    12/2016

OTHER PUBLICATIONS

Yang, C.-W. et al. Cell 164:141-155 (Jan. 2016). (Year: 2016).*
Campbell, C.D. et al. PLOS One 9(8):e104396. Aug. 2014. (Year: 2014).*
Sleiman, P.M.A. et al. New England Journal of Medicine 362(1):36. (Jan. 2010; online Dec. 2009). (Year: 2009).*
(Continued)

*Primary Examiner* — Diana B Johannsen
(74) *Attorney, Agent, or Firm* — Kathleen D. Rigaut; Howson & Howson LLP

(57) ABSTRACT

Compositions and methods for diagnosing and treating asthma and asthma patients a Th2 high asthma phenotype are disclosed.

10 Claims, 13 Drawing Sheets

Specification includes a Sequence Listing.

Genes Implicated in Asthma Pathogenesis

(56) References Cited

OTHER PUBLICATIONS

International Search Report, dated Jun. 1, 2018, for International Application No. PCT/US2018/012963, filed Jan. 9, 2018.
Bhakta, Nirav R. et al., "A qPCR-based metric of Th2 airway inflammation in asthma," Clinical and Translational Allergy, vol. 3, No. 1, 2013, pp. 1-9.
Gehin, Martine et al., "A Novel CRTH2 Antagonist: Single- and Multiple-Dose Tolerability, Pharmacokinetics, and Pharmacodynamics of ACT-453859 in Healthy Subjects," Journal of Clinical Pharmacology, vol. 55, No. 7, 2015, pp. 1-30.
Extended European Search Report, dated Sep. 25, 2020, issued in corresponding European Patent Application No. 18736650.5.
Gunawardhana, Lakshitha P. et al., "Differential DNA Methylation Profiles of Infants Exposed to Maternal Asthma During Pregnancy," Pediatric Pulmonology, vol. 49, No. 9, 2014, pp. 852-862.
Benson, Kiara K. et al., "Natural human genetic variation determines basal and inducible expression of PM20D1, an obesity-associated gene," PNAS, vol. 116, No. 46, 2019, pp. 23232-23242.
Wenzel, Sally E., "Asthma phenotypes: the evolution from clinical to molecular approaches," Nature Medicine, vol. 18, No. 5, 2012, pp. 716-725.
Woodruff, Prescott G. et al., "T-helper Type 2-driven Inflammation Defines Major Subphenotypes of Asthma," American Journal of Respiratory and Critical Care Medicine, vol. 180, No. 5, 2009, pp. 388-395.
Langie, Sabine A. S. et al., "Whole-Genome Saliva and Blood DNA Methylation Profiling in Individuals with a Respiratory Allergy," PLoS ONE, vol. 11, No. 3, 2016, e0151109, pp. 1-17.
Long Jonathan Z., "The secreted enzyme PM20D1 regulates lipidated amino acid uncouplers of mitochondria," Cell, vol. 166, No. 2, 2016, pp. 424-435.
Romagnani, Sergio, "Th1/Th2 cells," Inflammatory Bowel Diseases, vol. 5, No. 4, 1999, pp. 285-294.

* cited by examiner

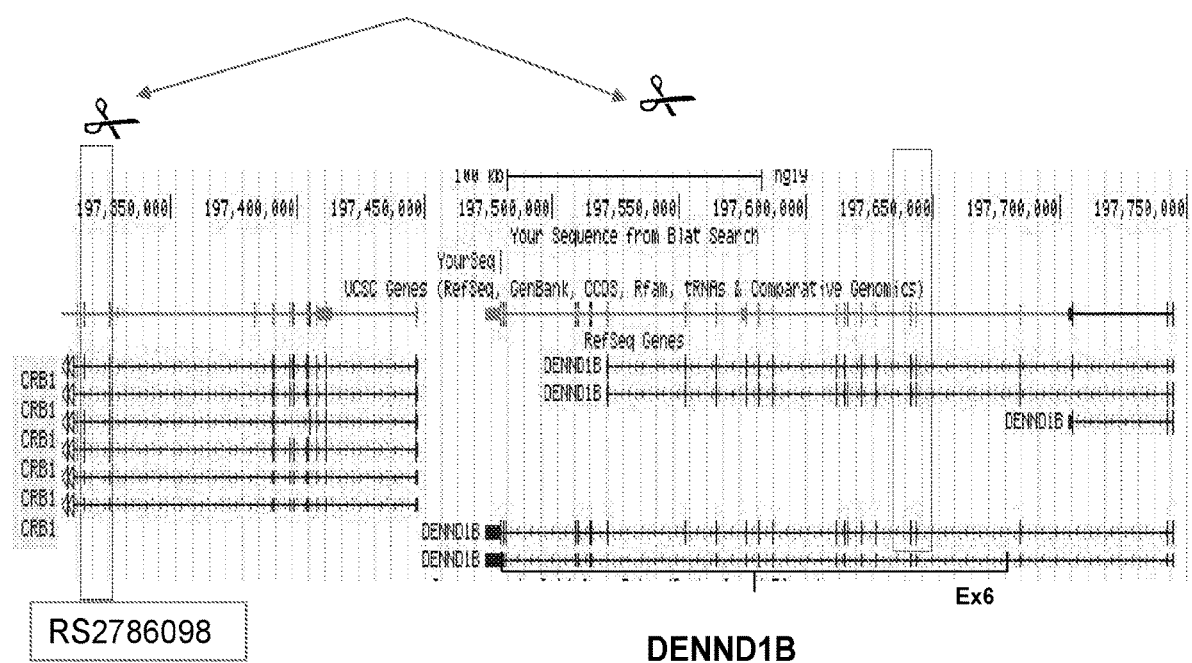
FIG. 2B CRISPR/Cas9 targeting DENND1b exon6 or rs2786098

*In vitro* Differentiation of human T cells from PBMCs
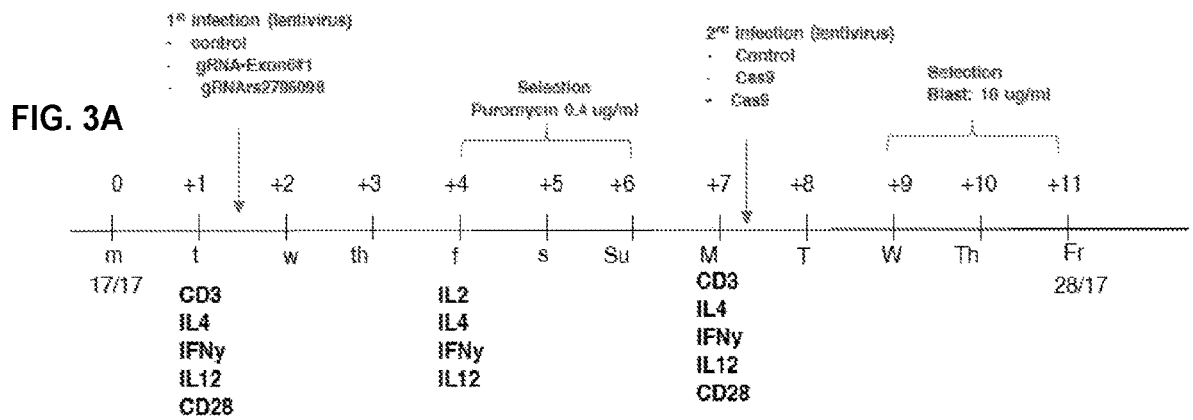
FIG. 3A
CRISPR of the rs2786098 SNP out or depletion of *DENND1b* increases expression of Th2 markers on T cells after Th2 differentiation
FIG. 3B
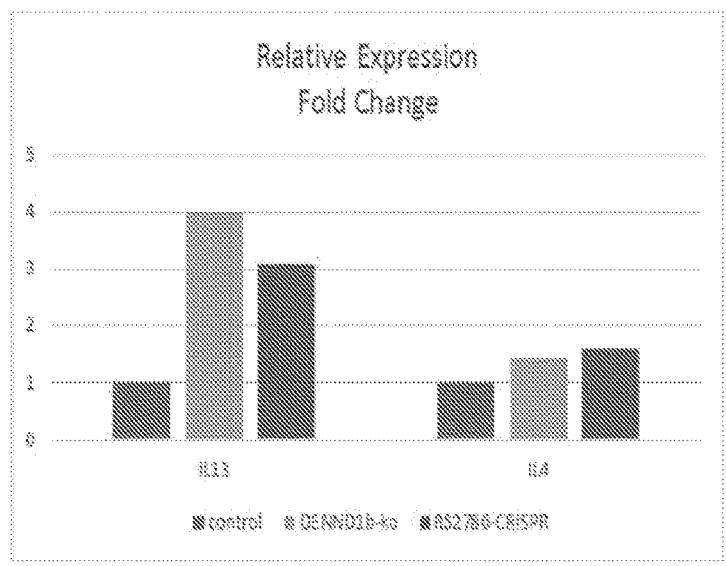

FIG. 5B

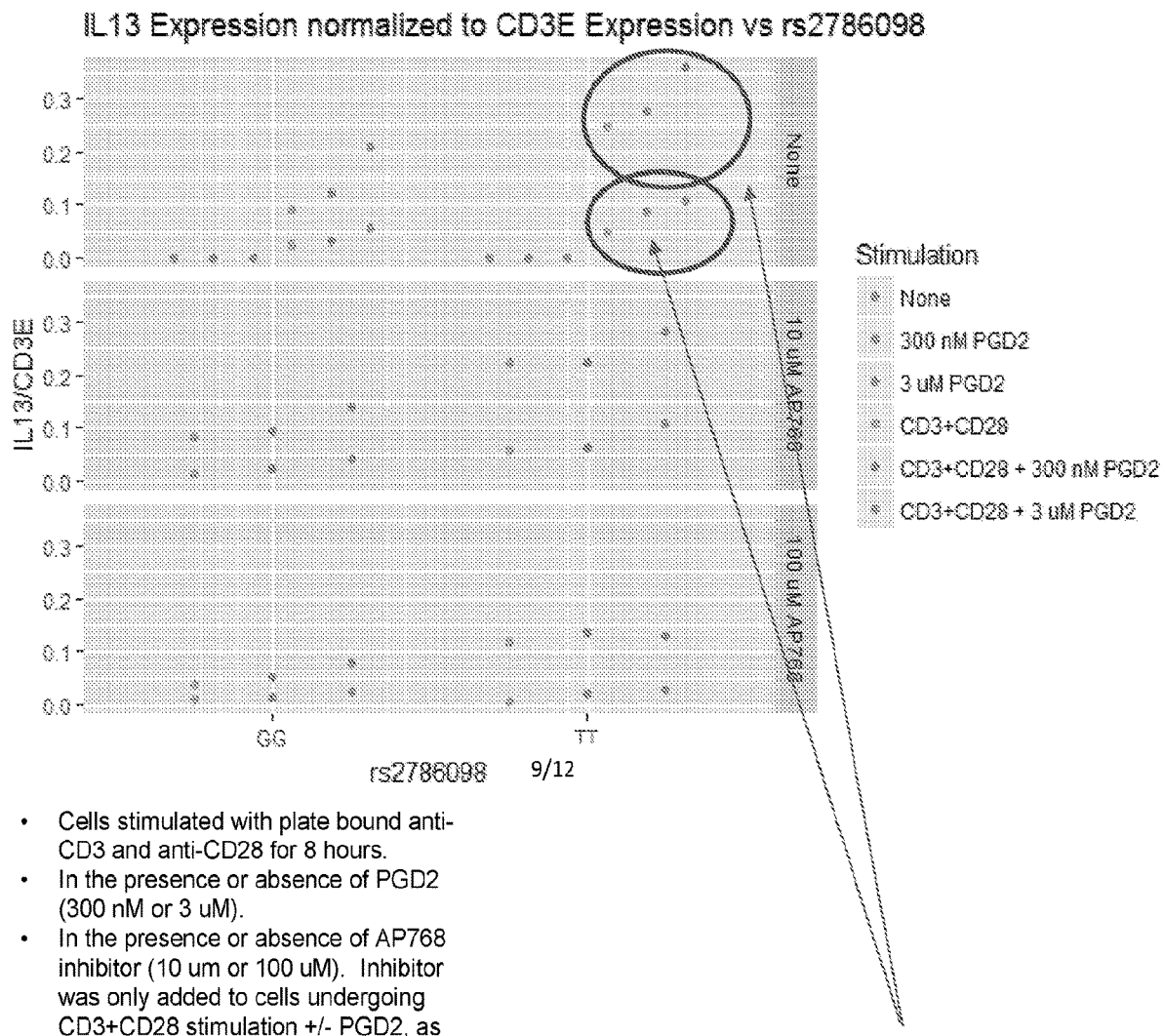

Two separate subjects, under different stimulation conditions

- Cells stimulated with plate bound anti-CD3 and anti-CD28 for 8 hours.
- In the presence or absence of PGD2 (300 nM or 3 uM).
- In the presence or absence of AP768 inhibitor (10 um or 100 uM). Inhibitor was only added to cells undergoing CD3+CD28 stimulation +/- PGD2, as no cytokines are produced without CD3 stimulation
- The different colors are the stimulation conditions (No stimulation, PGD2 alone, CD3+CD28, CD3+CD28+PGD2).
- There are 4 subjects total in this experiment. Each subject was stimulated in 6 different ways.
- The different vertical groups are different concentrations of AP768.
- Graphs are split based on DENND1B genotype Surface Staining for CRTH2 on expanded T cells Genes Implicated in Asthma Pathogenesis 
COMPOSITIONS AND METHODS TARGETING THE TH2 PATHWAY FOR THE TREATMENT OF ASTHMA This application is a § 371 national phase entry of PCT/US2018/012963 filed Jan. 9, 2018, which claims priority to U.S. Provisional Application Nos. 62/444,255 and 62/607,269 filed Jan. 9, 2017 and Dec. 18, 2017 respectively. Each of these applications are incorporated herein by reference as though set forth in full.

FIELD OF THE INVENTION

This invention relates to the fields of personalized medicine and targeted therapies based on epistatic genetic interactions observed in a subset of Th2-high asthmatic subjects.

INCORPORATION BY REFERENCE OF MATERIAL SUBMITTED IN ELECTRONIC FORM

Applicant hereby incorporates by reference the Sequence Listing material filed in electronic form herewith. The file is labelled "SEQLIST.txt", dated Dec. 27, 2021 and is 2,054 bytes in size.

BACKGROUND OF THE INVENTION

Several publications and patent documents are cited in this application in parentheses in order to further describe the state of the art to which the invention pertains. Each of these references is incorporated herein by reference as though set forth in full.

The Global Initiative for Asthma (GINA) defines asthma as "a heterogeneous disease, usually characterized by chronic airway inflammations associated with a history of respiratory symptoms such as wheeze, shortness of breath, chest tightness and cough that vary over time and in intensity, together with variable expiratory airflow limitation".

Several lines of evidence suggest that the underlying heterogeneity extends to the very basis of the disease. In 2009, Woodruff et al., (2) showed that asthmatics can be separated into at least two distinct molecular phenotypes defined by the degree of T-helper type 2 (Th2) inflammation in the airway. Th2 inflammation is mediated by IL-4, IL-5, and IL-13 and was until then considered the central molecular mechanism underlying all asthma. The subgroups, which they termed "Th2-high" and "Th2-low", not only differed in markers of inflammation but also response to therapy.

Clinical trials of highly specific therapies in asthma such as monoclonal antibodies for anti-interleukin (IL)-5, anti-IL-13 and anti-IL-4 receptor a (anti-IL-4Rα), have further highlighted that these highly specific therapies are generally more efficacious in groups of patients selected on the bases of target mechanism or pathway activation.

Currently, response to asthma therapy is determined by blood eosinophil counts and serum IgE measurement. However, these measures can be affected by environmental variables such as bacterial or viral infection and seasonal allergens that make classification imprecise. Clearly a need exists to identify genetic interactions involved in the manifestation of the asthmatic phenotype, particularly pediatric onset asthma. Such knowledge will facilitate diagnosis of this condition as well as provide new targets for the development of potent therapeutics for the treatment of asthma.

SUMMARY OF THE INVENTION

In accordance with the present invention, compositions and methods are provided for identifying asthma biomarkers as well as identifying biomarkers that identify asthma patients as having a Th2-high molecular phenotype. The biomarkers may be used in methods for diagnosing asthma patients, as well as in methods for diagnosing asthma patients having a Th2-high molecular phenotype. Methods are also provided for detecting combinations of single nucleotide polymorphisms (snps), and methods for identifying patients most likely to benefit from certain targeted therapies. Methods of treating subjects having such biomarkers are also disclosed. Such biomarkers can also be used to advantage for predicting response to asthma therapy.

In some embodiments, methods for diagnosing and treating asthma, including Th2-high molecular phenotype asthma are provided comprising detecting a combination of snps, wherein one snp is in the DENN1B gene and another snp is in the PM20D1 gene, wherein if the combination is detected, the subject has a Th2-high molecular phenotype asthma and can be treated with an agent that targets the Th2 inflammation pathway. The agent that targets the Th2 inflammation pathway may be a CRTH2 inhibitor. The CRTH2 inhibitor may be one or more agents from Table 2, such as, for example AP768 and/or AP770. In some embodiments, the DENN1B snp is rs2786098. In some embodiments the PM20D1 snp is selected from rs2014202, rs7522056, rs6673687, rs11240565, rs11240554, rs823116, rs1775146, rs1775143, rs12565321, and rs12567894. In some embodiments, the DENN1B and PM20D1 combination is selected from:
 a. rs2786098 and rs2014202,
 b. rs2786098 and rs7522056,
 c. rs2786098, rs2014202 and rs7522056,
 d. rs2786098 and rs6673687,
 e. rs2786098 and rs11240565,
 f. rs2786098 and rs11240554,
 g. rs2786098 and rs823116,
 h. rs27860798 and rs1775146,
 i. rs2786098 and rs1775143,
 j. rs2786098 and rs12565321, and
 k. rs2786098 and rs12567894.

In some embodiments, a method of diagnosing a human subject as having asthma, or diagnosing a human asthma subject as having asthma with a Th2-high molecular phenotype, is provided comprising determining whether the patient has a combination of single nucleotide polymorphisms (SNPs) selected from 1) rs2786098 and rs2014202, or 2) rs2786098 and rs7522056, and if present, diagnosing the subject as having asthma, or as having asthma with a Th2-high molecular phenotype. In some embodiments, a method of predicting whether an asthma patient has a Th2-high molecular phenotype is provided comprising determining whether the patient has a combination of single nucleotide polymorphisms (SNPs) selected from 1) rs2786098 and rs2014202, or 2) rs2786098 and rs7522056, and if present, predicting that the asthma patient has a Th2-high molecular phenotype.

In some embodiments, a method of treating an asthma patient having a Th2-high molecular phenotype is provided.

In some embodiments, a method for identifying a Th2 high molecular phenotype in a human asthma patient is provided comprising,
 a) obtaining a biological sample comprising nucleic acids from a human asthma patient; and
 b) detecting in said sample, nucleic acids harboring a combination of single nucleotide polymorphisms (SNPs) selected from 1) rs2786098 and rs2014202, or 2) rs2786098 and rs7522056, thereby identifying a Th2 high molecular phenotype in said patient. In some embodiments, rs2786098 and rs2014202 function epistatically. In some embodiments, the method further comprises administering an agent that targets the Th2 inflammation pathway. The agent that targets the Th2 inflammation pathway may be a CRTH2 inhibitor. The CRTH2 inhibitor may be one or more agents from Table 2, such as, for example AP768 and/or AP770.

In some embodiments, a method for identifying a Th2 high molecular phenotype in an asthma patient is provided comprising,
  a) obtaining a biological sample comprising nucleic acids from said patient; and
  b) detecting in said sample, nucleic acids harboring a single nucleotide polymorphisms (SNPs) rs2786098 and rs7522056, thereby identifying a Th2 high molecular phenotype in said patient. In some embodiments, rs2786098 and rs7522056 function epistatically. In some embodiments, the method further comprises administering one or more agents from Table 2, such as, for example AP768 and/or AP770.

The methods may further comprise detection of one or more of nucleic acids harboring single nucleotide polymorphism (SNP) having rs numbers selected from rs6673687, rs11240565, rs11240554, rs823116, rs1775146, rs1775143, rs12565321, and rs12567894. In certain embodiments, the risk allele is detected, indicating that the subject is at increased risk for asthma. In other embodiments, the protective allele is detected, indicating that the subject is not at increased risk.

In some embodiments, methods for identifying a subject as having asthma, or asthma with a Th2 high molecular phenotype are provided comprising,
  a) obtaining a biological sample comprising nucleic acids from said patient; and
  b) detecting in said sample, nucleic acids harboring any of the following combinations of single nucleotide polymorphisms (SNPs):
    a. rs2786098 and rs2014202,
    b. rs2786098 and rs7522056,
    c. rs2786098, rs2014202 and rs7522056,
    d. rs2786098 and rs6673687,
    e. rs2786098 and rs11240565,
    f. rs2786098 and rs11240554,
    g. rs2786098 and rs823116,
    h. rs27860798 and rs1775146,
    i. rs2786098 and rs1775143,
    j. rs2786098 and rs12565321,
    k. rs2786098 and rs12567894,
and identifying the subject as having asthma, or asthma with a Th2 high molecular phenotype if any one or more combinations are identified. In some embodiments, the method further comprises administering one or more agent of Table 2 to the identified subject. In some embodiments, the agent is AP768. In some embodiments, the agent is AP770.

In some embodiments, the invention comprises a method of diagnosing a subject as having asthma comprising,
  a) obtaining a biological sample comprising nucleic acids from said patient; and
  b) detecting in said sample, nucleic acids harboring a single nucleotide polymorphism (SNPs) in any one or more of SNPs rs2014202, rs7522056, rs6673687, rs11240565, rs11240554, rs823116, rs1775146, rs1775143, rs12565321, and rs12567894, thereby diagnosing asthma in said patient.

In some embodiments, the invention comprises a method of diagnosing a subject as having asthma comprising
  a) obtaining a biological sample comprising nucleic acids from said patient, or analyzing information derived from a review of a subject's nucleic acid, to determine the presence or absence of:
    i) any one or more of SNPs rs2014202, rs7522056, rs6673687, rs11240565, rs11240554, rs823116, rs1775146, rs1775143, rs12565321, and rs12567894; and
    ii) rs2786098, wherein the presence indicates the patient has asthma.

In some embodiments, the subject/patient identified as having asthma is administered any one or more of the agents of Table 2. In certain embodiments, the agent is AP768.

In some embodiments, the presence of the polymorphisms identify a subject/patient as having asthma as Th2-high asthma.

In any of the diagnostic methods described herein, the SNP may be detected by performing a process selected from detection of specific hybridization, measurement of allele size, restriction fragment length polymorphism analysis, allele-specific hybridization analysis, single base primer extension reaction, and sequencing of an amplified polynucleotide. The target nucleic acid may be amplified prior to detection.

The nucleic acids comprising said polymorphism may be obtained from isolated cells from a human subject.

In some embodiments, the invention comprises a method for treating an asthma patient having a Th2 high molecular phenotype, comprising;
  a) obtaining a biological sample comprising nucleic acids from said patient, or obtaining genetic information from the patient; and
  b) detecting in said sample, or identifying in said genetic information, at least two nucleic acids harboring a single nucleotide polymorphism (SNP) selected from rs2786098 and rs2014202, or rs2786098 and rs7522056 thereby identifying a Th2 high molecular phenotype in said patient; and
  c) treating said patient with an agent that targets the Th2 inflammation pathway. The agent may be any one of the agents recited in Table 2. In some embodiments, rs2786098 and rs2014202 function epistatically. In some embodiments, rs2786098 and rs7522056 function epistatically.

In some embodiments, the method of treatment further comprises detecting of one or more of nucleic acids harboring single nucleotide polymorphism (SNP) having rs numbers selected from rs6673687, rs11240565, rs11240554, rs823116, rs1775146, rs1775143, rs12565321, and rs12567894.

In some embodiments, the invention comprises a method of treating asthma comprising administering any of the agents of Table 2 to a subject having:
  1) any one or more of SNPs rs2014202, rs7522056, rs6673687, rs11240565, rs11240554, rs823116, rs1775146, rs1775143, rs12565321, and rs12567894; or
  2) rs2786098 together with any one or more of SNPs: rs2014202, rs7522056, rs6673687, rs11240565, rs11240554, rs823116, rs1775146, rs1775143, rs12565321, and rs12567894.

In some embodiments, the invention comprises a method of treating an asthma patient having a Th2 high molecular phenotype comprising administering any of the agents of Table 2 to a subject having:

1) any one or more of SNPs rs2014202, rs7522056, rs6673687, rs11240565, rs11240554, rs823116, rs1775146, rs1775143, rs12565321, and rs12567894; or
2) rs2786098 together with any one or more of SNPs: rs2014202, rs7522056, rs6673687, rs11240565, rs11240554, rs823116, rs1775146, rs1775143, rs12565321, and rs12567894.

In some embodiments, the invention comprises a method for treating asthma in a human subject, comprising,
   a) obtaining genetic information relating to the subject;
   b) determining from the genetic information whether the subject has:
      i) any one or more of SNPs rs2014202, rs7522056, rs6673687, rs11240565, rs11240554, rs823116, rs1775146, rs1775143, rs12565321, and rs12567894; or
      ii) rs2786098 together with any one or more of SNPs: rs2014202, rs7522056, rs6673687, rs11240565, rs11240554, rs823116, rs1775146, rs1775143, rs12565321, and rs12567894; and
   c) administering an effective amount of any one or more of the agents of Table 2 to the subject if it is determined that the subject satisfies part i) or ii), thereby treating asthma. In some embodiments, the subject has a Th2-high asthma phenotype. In certain embodiments, the subject is treated with AP768.

In some embodiments, a method of treating asthma is provided comprising administering one or more agent of Table 2 to a subject having rs2786098 and rs2014202, or rs2786098 and rs7522056.

BRIEF DESCRIPTION OF THE DRAWINGS

FIG. 2B demonstrates excision of the lead SNP using CRISPR/Cas9.

FIGS. 3A and 3B. Effects on TH2 cytokine expression was examined in the presence and absence of DENND1B knock out and after excision of the lead DENND1B SNP, rs2786098, using CRISPR. T cell differentiation was performed as previously described (FIG. 3A). Expression of IL13 and IL4 is increased following DENND1B KO and following excision of rs2786098 using CRISPR, indicating that DENND1B regulates the expression of TH2 cytokines and the expression regulation is largely attributed to the actions of rs2786098 (FIG. 3B).

FIGS. 5A and 5B. FIG. 5A: T cells from healthy human volunteers were stimulated with 300 nM PGD2 in the presence or absence of CD3/CD28 stimulation. Stimulation occurred in the presence of increasing concentrations of the CRTH2 inhibitor AP768. Inhibition of IL13 production was observed, indicating that the IL13 production is mediated through the CRTH2 receptor and is inhibited at increasing concentrations of the inhibitor. FIG. 5B:

FIG. 8B shows the pathways and genes implicated in asthma pathogenesis.

DETAILED DESCRIPTION OF THE INVENTION

Figure 1:
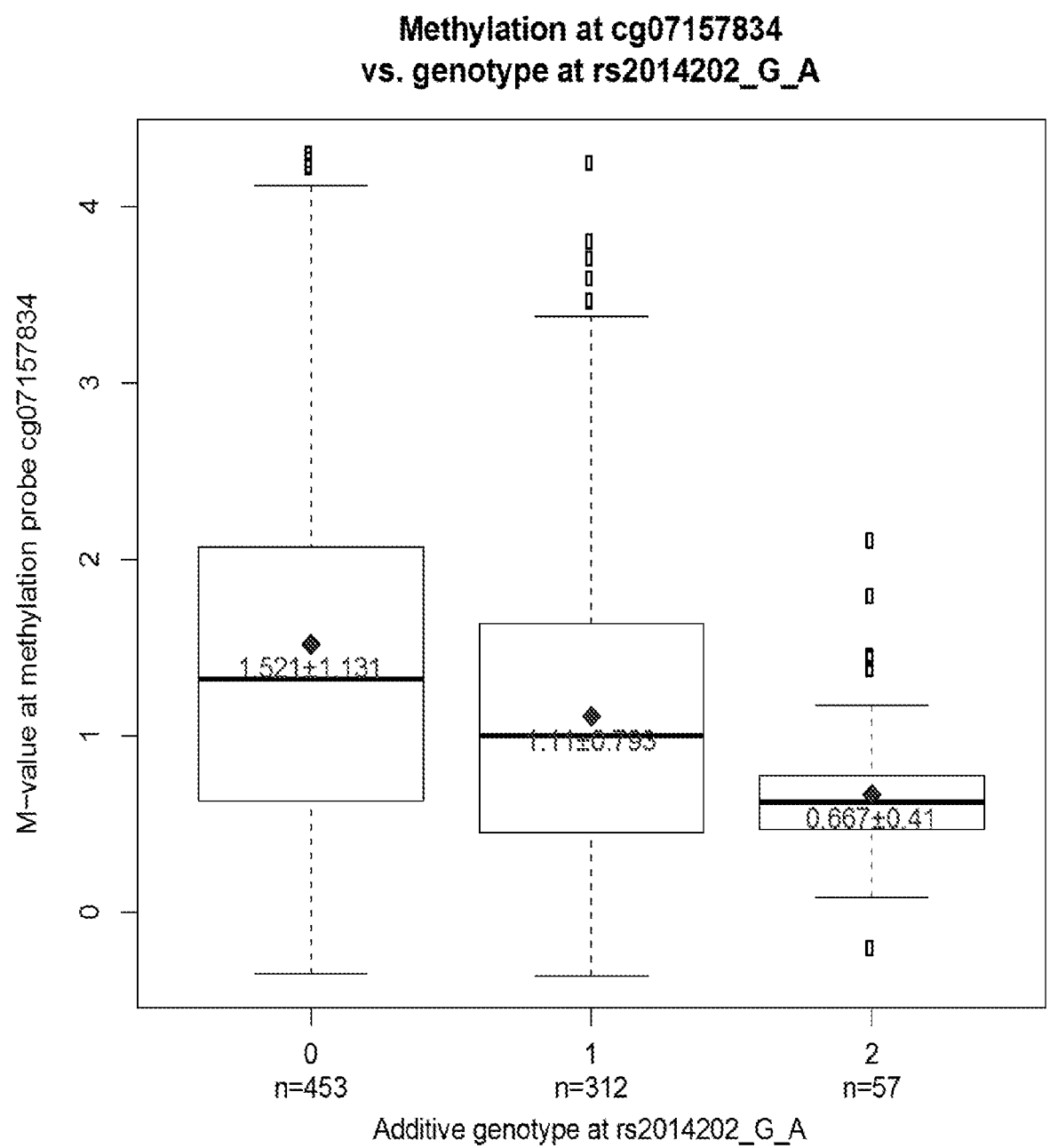
FIG. 1 shows the methylation status at PM20D1 (M-value on y-axis) correlates with rs2014202 genotype (x-axis 0=homozygous wild type, 1=heterozygote, 2=homozygote (minor allele)).

The DENN domain is an evolutionary conserved protein module found in all eukaryotes and serves as an exchange factor for Rab-GTPases to regulate diverse cellular functions. Variants in DENND1B are associated with development of childhood asthma and other immune disorders (3). In other studies, Dennd1b-/-mice were generated which exhibit hyper-allergic responses following antigen challenge. Dennd1b-/-TH2 cells, but not other TH cells, exhibit delayed receptor-induced T cell receptor (TCR) down-modulation, enhanced TCR signaling, and increased production of effector cytokines. Notably, TH2 cells carrying asthma-associated DENND1B variants express less DENND1B and phenocopy Dennd1b-/-TH2 Cells (4). These results provide a molecular basis for how DENND1B, a previously unrecognized regulator of TCR down-modulation in TH2 cells, contributes to asthma pathogenesis and how DENN-domain containing proteins may contribute to other human disorders. See Yang et al. (4).

A large body of evidence indicates the existence of functionally polarized CD4+ T-cell responses based on their profile of cytokine secretion. Type 1 T helper (Th1) cells produce interferon-gamma, interleukin (IL)-2, and tumor necrosis factor (TNF)-beta, which activate macrophages and are responsible for cell-mediated immunity and phagocyte-dependent protective responses. By contrast, type 2 Th (Th2) cells produce IL-4, IL-5, IL-10, and IL-13, which are responsible for strong antibody production, eosinophil activation, and inhibition of several macrophage functions, thus providing phagocyte-independent protective responses. Th1 cells mainly develop following infections by intracellular bacteria and some viruses, whereas Th2 cells predominate in response to infestations by gastrointestinal nematodes.

Polarized Th1 and Th2 cells not only exhibit different functional properties, but also show the preferential expression of some activation markers and distinct transcription factors. Several mechanisms may influence the Th cell differentiation, which include the cytokine profile of "natural immunity" evoked by different offending agents, the nature of the peptide ligand, as well as the activity of some costimulatory molecules and microenvironmentally secreted hormones, in the context of the individual genetic background. In addition to playing different roles in protection, polarized Th1-type and Th2-type responses are also responsible for different types of immunopathological reactions (8).

Prostaglandin D2 (PGD2) regulates various immunological responses via two distinct PGD2 receptors, prostaglandin D receptor (DP), and chemoattractant receptor-homologous molecule expressed on Th2 cells (CRTH2). The present invention is based on data presented hereinbelow indicating that asthma subjects and other subjects who exhibit greater Th2 pathway responses, and/or biomarkers, are more likely to obtain therapeutic benefit from agents which block CRTH2. The present inventors have identified risk variants in DENND1B and PM20D1 which can be used to identify such subjects, which in turn would indicate CRTH2 inhibitors should alleviate asthmatic symptoms and provide therapeutic benefit.

DEFINITIONS

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

"Th2 high asthma-associated SNP or specific marker" is a SNP or marker which is associated with a Th2 high molecular phenotype. Such markers may include but are not limited to nucleic acids, proteins encoded thereby, or other small molecules.

A "Th2-high asthma molecular phenotype" also referred to herein as "Th2 high molecular phenotype" or "Th2-high" asthma or the like refers to the Th2 high molecular phenotype described by Woodruff et al. (3). For example, a Th2-high asthma indicates that the subject has the propensity to respond to asthma triggers by making Th2 cytokines such as IL-4, IL-5, and IL-13 (rather than Th1 cytokines such as IL-2, IL-12 and IFN-γ). The TH2 high phenotype is also often associated with elevated IgE levels and elevated eosinophil counts in serum or plasma.

A "single nucleotide polymorphism (SNP)" refers to a change in which a single base in the DNA differs from the usual base at that position. These single base changes are called SNPs or "snips." Millions of SNP's have been cataloged in the human genome. Some SNPs such as that which causes sickle cell are responsible for disease. Other SNPs are normal variations in the genome. SNPs present in a nucleic acid oligomer are often identified by "rs" numbers. The SNP and flanking sequences comprising the SNP can be found in the publicly available SNP database, dbSNP by entering the "rs" number into the search bar on the website.

Risk alleles for common complex diseases are usually defined by the minor, or least common, allele frequency (MAF). This allows for differentiation between common and rare alleles in the population. The MAF of common risk alleles can range from 5% to 50%. The risk alleles for the SNPs described herein are provided in Tables 1A and 1B.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

"Linkage" describes the tendency of genes, alleles, loci or genetic markers to be inherited together as a result of their location on the same chromosome, and is measured by percent recombination (also called recombination fraction, or θ) between the two genes, alleles, loci or genetic markers. The closer two loci physically are on the chromosome, the lower the recombination fraction will be. Normally, when a polymorphic site from within a disease-causing gene is tested for linkage with the disease, the recombination fraction will be zero, indicating that the disease and the disease-causing gene are always co-inherited. In rare cases, when a gene spans a very large segment of the genome, it may be possible to observe recombination between polymorphic sites on one end of the gene and causative mutations on the other. However, if the causative mutation is the polymorphism being tested for linkage with the disease, no recombination will be observed.

"Centimorgan" is a unit of genetic distance signifying linkage between two genetic markers, alleles, genes or loci, corresponding to a probability of recombination between the two markers or loci of 1% for any meiotic event.

"Linkage disequilibrium" or "allelic association" means the preferential association of a particular allele, locus, gene or genetic marker with a specific allele, locus, gene or genetic marker at a nearby chromosomal location more frequently than expected by chance for any particular allele frequency in the population. Once a known SNP is identified, SNPs in linkage disequilibrium (also termed LD) may be identified via commercially available programs. For example, on the world wide web at analysistools.nci.nih.gov/LDlink/?tab=ldproxy. First, the LDproxy tab is selected. The reference rs number is entered, the r2 tab and the population of interest are selected and the SNPs in LD identified upon clicking on the "calculate" tab. A plot of surrounding area is revealed and a table with the SNPs in LD (with r2 values) is shown.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

"Target nucleic acid" as used herein refers to a previously defined region of a nucleic acid present in a complex nucleic acid mixture wherein the defined wild-type region contains at least one known nucleotide variation which may or may not be associated with asthma. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. Thus, the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus, if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any asthma specific marker nucleic acid, but does not hybridize to other nucleotides. Also polynucleotide which "specifically hybridizes" may hybridize only to an airway specific marker, such as an asthma-specific marker shown in the Tables contained herein. Appropriate conditions enabling specific hybridization of single stranded nucleic acid molecules of varying complementarity are well known in the art. For instance, one common formula for calculating the stringency conditions required to achieve hybridization between nucleic acid molecules of a specified sequence homology is set forth below (Sambrook et al., Molecular Cloning, Cold Spring Harbor Laboratory (1989):

$$T_m = 81.5\text{"}C + 16.6 \text{ Log } [Na+] + 0.41(\% \ G+C) - 0.63(\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57"C. The $T_m$ of a DNA duplex decreases by 1-1.5"C with every 1% decrease in homology. Thus, targets with greater than about 75% sequence identity would be observed using a hybridization temperature of 42"C. The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length. An oligonucleotide can comprise a single nucleotide polymorphism within its sequence. For example, oligonucleotides comprising the SNP indicated by the rs number rs2786098 are found in the SNP data base. Typing the indicated rs number into the SNP database will reveal a sequence comprising the SNPs and as well as short flanking sequences. Such sequences are useful as oligonucleotide probes and primers as described hereinbelow.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

A "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, CA, USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting DENN/D1B mRNA, for example, are known in the art and may be between 15-35 nucleotides in length, and more typically about 21 nucleotides in length.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and Atransduction@ refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the asthma specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the asthma specific marker encoding nucleic acid. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

"Sample" or "patient sample" or "biological sample" generally refers to a sample which may be tested for a particular molecule, preferably an asthma specific marker molecule, such as a marker provided below. Samples may include but are not limited to cells, body fluids, including blood, serum, sputum, plasma, urine, saliva, tears, pleural fluid and the like.

The terms "agent" and "test compound" are used interchangeably herein and denote a chemical compound, small molecule, a mixture of chemical compounds, a biological macromolecule, or an extract made from biological materials such as bacteria, plants, fungi, or animal (particularly mammalian) cells or tissues. Biological macromolecules include antibodies, siRNA, shRNA, antisense oligonucleotides, peptides, peptide/DNA complexes, and any nucleic acid based molecule which exhibits the capacity to modulate the activity of the SNP containing nucleic acids described herein or their encoded proteins. Agents are evaluated for potential biological activity by inclusion in screening assays described hereinbelow.

"Treatment" as used herein, covers any administration or application of a therapeutic for disease in a mammal, including a human, and includes inhibiting the disease or progression of the disease, inhibiting or slowing the disease or its progression, arresting its development, partially or fully relieving the disease, preventing the onset of the disease, or preventing a recurrence of symptoms of the disease. Example treatments include administration of the agents listed in Table 2 at efficacious doses.

In some embodiments, a method of diagnosing a subject as having asthma is provided comprising analyzing nucleic acid from a subject, or analyzing information derived from a review of a subject's nucleic acid, to determine the presence or absence of any one or more of SNPs rs2014202, rs7522056, rs6673687, rs11240565, rs11240554, rs823116, rs1775146, rs1775143, rs12565321, and rs12567894. In some embodiments, the method comprises analyzing nucleic acid from a subject, or analyzing information derived from a review of a subject's nucleic acid, to determine the presence or absence of:

1) any one or more of SNPs rs2014202, rs7522056, rs6673687, rs11240565, rs11240554, rs823116, rs1775146, rs1775143, rs12565321, and rs12567894; and
2) rs2786098.

The presence of any one or more of SNPs rs2014202, rs7522056, rs6673687, rs11240565, rs11240554, rs823116, rs1775146, rs1775143, rs12565321, and rs12567894 alone, or in combination with rs2786098, is indicative of asthma. A subject identified as having asthma by this method may be administered any of the agents of Table 2. In some embodiments, the agent is AP768 or AP770.

In some embodiments, a method of diagnosing a subject as having Th2-high asthma is provided comprising analyzing nucleic acid from a subject, or analyzing information derived from a review of a subject's nucleic acid, to determine the presence or absence of any one or more of SNPs rs2014202, rs7522056, rs6673687, rs11240565, rs11240554, rs823116, rs1775146, rs1775143, rs12565321, and rs12567894. In some embodiments, the method comprises analyzing nucleic acid from a subject, or analyzing information derived from a review of a subject's nucleic acid, to determine the presence or absence of 1) any one or more of SNPs rs2014202, rs7522056, rs6673687, rs11240565, rs11240554, rs823116, rs1775146, rs1775143, rs12565321, and rs12567894; and
2) rs2786098.

The presence of any one or more of SNPs rs2014202, rs7522056, rs6673687, rs11240565, rs11240554, rs823116, rs1775146, rs1775143, rs12565321, and rs12567894 alone, or in combination with rs2786098, is indicative of Th2-high asthma. Once identified, these subjects can be effectively treated with any of the agents of Table 2. In some embodiments, the agent is AP768 or AP770.

In some embodiments, methods of treating asthma and Th2-high asthma are provided comprising administering any of the agents of Table 2 to a subject having:

1) any one or more of SNPs rs2014202, rs7522056, rs6673687, rsl 1240565, rs11240554, rs823116, rs1775146, rs1775143, rs12565321, and rs12567894; or
2) rs2786098 together with any one or more of SNPs: rs2014202, rs7522056, rs6673687, rs11240565, rs11240554, rs823116, rs1775146, rs1775143, rs12565321, and rs12567894.

In some embodiments, methods of treating asthma and Th2-high asthma in human subjects are provided, comprising, a) obtaining genetic information relating to the subject or obtaining a biological sample comprising nucleic acid;
b) determining from the genetic information or biological sample whether the subject has:
   i) any one or more of SNPs rs2014202, rs7522056, rs6673687, rs11240565, rs11240554, rs823116, rs1775146, rs1775143, rs12565321, and rs12567894; or
   ii) rs2786098 together with any one or more of SNPs: rs2014202, rs7522056, rs6673687, rs11240565, rs11240554, rs823116, rs1775146, rs1775143, rs12565321, and rs12567894; and
c) administering an effective amount of any one or more of the agents of Table 2 to the subject if it is determined that the subject satisfies part i) or ii), thereby treating asthma or Th2-high asthma.

SNP containing nucleic acids, including but not limited to those listed in Table 1 and the Examples (sometimes referred to herein as "asthma-associated SNP(s)" or "Th2-high asthma associated SNP(s)") may be used for a variety of purposes in accordance with the present invention. Asthma-associated SNP containing DNA, RNA, or fragments thereof may be used as probes or primers to detect the presence of and/or expression of asthma specific markers. Methods in which asthma specific marker nucleic acids may be utilized as probes or primers for such assays include, but are not limited to: (1) in situ hybridization; (2) Southern hybridization (3) northern hybridization; and (4) assorted amplification reactions such as polymerase chain reactions (PCR) or qPCR.

Further, assays for detecting asthma-associated SNPs or the proteins encoded thereby may be conducted on any type of biological sample, including but not limited to body fluids (including blood, sputum, urine, serum, bronchial lavage), any type of cell (such as lung cells, airway smooth muscle cells, white blood cells, mononuclear cells) or body tissue.

From the foregoing discussion, it can be seen that the asthma-associated SNP containing nucleic acids associated with a Th2 high phenotype, vectors expressing the same, asthma SNP containing marker proteins and anti-asthma specific marker antibodies of the invention can be used to detect asthma associated SNPs in body tissue, cells, or fluid, and alter asthma SNP containing marker protein expression for purposes of assessing the genetic and protein interactions involved in the development of asthma.

In most embodiments for screening for Th2-high asthma-associated SNPs, the asthma-associated SNP containing nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are becoming increasingly important in the art.

Alternatively, new detection technologies can overcome this limitation and enable analysis of small samples containing as little as 1 g of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Thus, any of the aforementioned techniques may be used to detect or quantify Th2-high asthma-associated SNP marker expression and accordingly, diagnose asthma patients most likely to benefit from treatment protocols which target this pathway.

Any of the aforementioned products can be incorporated into a kit which may contain a Th2-high asthma-associated SNP specific marker polynucleotide or one or more such markers immobilized on a Gene Chip, an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof.

Identification of Asthmatic Patients and Asthmatic Patients Having a Th2-High Molecular Phenotype The information herein above can be applied clinically to patients for identifying, diagnosing, and predicting likelihood of having asthma and asthma with a Th2 high molecular phenotype, thereby streamlining therapeutic intervention approaches for such patients. Diagnostic compositions, including microarrays, and methods can be designed to identify nucleic acids harboring the SNPs described herein in nucleic acids from a patient to assess susceptibility for developing Th2-high molecular phenotype asthma. This can occur after a patient arrives in the clinic; the patient has blood drawn, and using the diagnostic methods described herein, a clinician can detect a SNP described herein. The information obtained from the patient sample, which can optionally be amplified prior to assessment, will be used to diagnose a patient with an increased or decreased susceptibility for developing Th2 high asthma. Kits for performing the diagnostic method of the invention are also provided herein. Such kits comprise a microarray comprising at least one of the SNPs provided herein in and the necessary reagents for assessing the patient samples as described above.

In some embodiments, methods for identifying a Th2 high molecular phenotype in a human asthma patient is encompassed comprising;
  a) obtaining a biological sample comprising nucleic acids from said a human asthma patient; and
  b) detecting in said sample, nucleic acids harboring a combination of single nucleotide polymorphisms (SNPs) selected from 1) rs2786098 and rs2014202, 2) rs2786098 and rs7522056, or 3) rs2786098 together with any one or more of rs6673687, rs11240565, rs11240554, rs823116, rs1775146, rs1775143, rs12565321, and rs12567894, thereby identifying a Th2 high molecular phenotype in said patient. In some embodiments, the combination of snps detected is rs2786098 and rs2014202. In some embodiments, the combination of snps detected is rs2786098 and rs7522056. In some embodiments, the combination of snps detected is rs2786098 and rs6673687. In some embodiments, the combination of snps detected is rs2786098 and rs11240565. In some embodiments, the combination of snps detected is rs2786098 and rs11240554. In some embodiments, the combination of snps detected is rs2786098 and rs823116. In some embodiments, the combination of snps detected is rs2786098 and rs1775146. In some embodiments, the combination of snps detected is rs2786098 and rs1775143. In some embodiments, the combination of snps detected is rs2786098 and rs12565321. In some embodiments, the combination of snps detected is rs2786098 and rs12567894.

In some embodiments, methods for diagnosing asthma are provided as are methods of diagnosing a human asthma patient as having an asthma with a Th2 high molecular phenotype comprising;
  a) obtaining a biological sample comprising nucleic acids from a human asthma patient; and
  b) detecting in said sample, nucleic acids harboring a combination of single nucleotide polymorphisms (SNPs) selected from 1) rs2786098 and rs2014202, 2) rs2786098 and rs7522056, or 3) rs2786098 together with any one or more of rs6673687, rs11240565, rs11240554, rs823116, rs1775146, rs1775143, rs12565321, and rs12567894, wherein if such combination is detected, said subject is diagnosed as having asthma and asthma with a Th2 high molecular phenotype. In some embodiments, the combination of snps detected is rs2786098 and rs2014202. In some embodiments, the combination of snps detected is rs2786098 and rs7522056. In some embodiments, the combination of snps detected is rs2786098 and rs6673687. In some embodiments, the combination of snps detected is rs2786098 and rs11240565. In some embodiments, the combination of snps detected is rs2786098 and rs11240554. In some embodiments, the combination of snps detected is rs2786098 and rs823116. In some embodiments, the combination of snps detected is rs2786098 and rs1775146. In some embodiments, the combination of snps detected is rs2786098 and rs1775143. In some embodiments, the combination of snps detected is rs2786098 and rs12565321. In some embodiments, the combination of snps detected is rs2786098 and rs12567894.

In some embodiments, no diagnosis is made, rather, what is encompassed is a method for detecting a combination of single nucleotide polymorphisms (SNPs) in a human biological sample comprising isolating nucleic acid from a human biological sample and contacting the sample with probes or primers of sufficient length and composition to detect a combination of snps selected from 1) rs2786098 and rs2014202, 2) rs2786098 and rs7522056, or 3) rs2786098 together with any one or more of rs6673687, rs11240565, rs11240554, rs823116, rs1775146, rs1775143, rs12565321, and rs12567894. In some embodiments, the combination of snps detected is rs2786098 and rs2014202. In some embodiments, the combination of snps detected is rs2786098 and rs7522056. In some embodiments, the combination of snps detected is rs2786098 and rs6673687. In some embodiments, the combination of snps detected is rs2786098 and rs11240565. In some embodiments, the combination of snps detected is rs2786098 and rs11240554. In some embodiments, the combination of snps detected is rs2786098 and rs823116. In some embodiments, the combination of snps detected is rs2786098 and rs1775146. In some embodiments, the combination of snps detected is rs2786098 and rs1775143. In some embodiments, the combination of snps detected is rs2786098 and rs12565321. In some embodiments, the combination of snps detected is rs2786098 and rs12567894.

In each identification and diagnostic method described herein, the method may further comprise administering a CRTH2 inhibitor to treat the asthma/Th2 high asthma. The CRTH2 inhibitor may be any CRTH2 inhibitor known, or any one or more of those selected from Table 2.

Methods for Treating Asthma and Th2-High Molecular Phenotype Asthma

In order to treat an individual having asthma and patients having a Th2 high molecular asthma phenotype, to alleviate a sign or symptom of the disease, suitable agents targeting the genes disclosed in Table 2 below can be administered alone or in combination in order to provide therapeutic benefit to the patient. Such agents will be administered in an effective dose to alleviate at least one symptom of asthma and/or Th2-high molecular phenotype asthma.

First, as described above, a biological sample, or genotyping information, is obtained from a patient. Genetic information gleaned from nucleic acids present in the sample would then be assessed for the presence or absence of the Th2-high molecular phenotype asthma SNP containing nucleic acids associated with this type of asthma. The presence of the risk allele SNP(s) indicating the presence of Th2-high molecular phenotype asthma, along with the simultaneous identification of the genes affected, provide the clinician with guidance as to which therapeutic agents are appropriate. The total treatment dose or doses (when two or more targets are to be modulated) can be administered to a subject as a single dose or can be administered using a fractionated treatment protocol, in which multiple/separate doses are administered over a more prolonged period of time, for example, over the period of a day to allow administration of a daily dosage or over a longer period of time to administer a dose over a desired period of time. One skilled in the art would know that the amount of Th2-high molecular phenotype asthma agent required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having Th2-high molecular phenotype asthma.

In an individual suffering from Th2-high molecular phenotype asthma, in particular a more severe form of the disease, administration of therapeutic agents can be particularly useful when administered in combination, for example, with a conventional agent for treating such a disease. The skilled artisan would administer Th2-high molecular phenotype asthma therapeutic agent(s) such as an agent that targets the Th2 inflammation pathway such as a CRTH2 inhibitor, such as any one or more of the agents shown in Table 2, alone or in combination with non-Table 2 asthma therapy, and would monitor the effectiveness of such treatment using routine methods such as pulmonary, and/or inflammatory function determination, radiologic, immunologic assays, or, where indicated, histopathologic methods. Other conventional agents for the treatment of asthma include steroid or administration of other agents that alleviate the symptoms underlying the disease.

Administration of the pharmaceutical preparation is preferably in an "effective amount" this being sufficient to show benefit to the individual. This amount prevents, alleviates, abates, or otherwise reduces the severity of asthmatic symptoms in a patient.

In some embodiments of this invention, a method is provided for the synergistic treatment of asthma using the pharmaceutical agents disclosed in Table 2 in combinatorial approaches. Advantageously, the synergistic method of this invention reduces the development of asthma, or reduces symptoms of asthma in a subject.

Methods for the safe and effective administration of most of these agents are known to those skilled in the art. In addition, their administration is described in the standard literature. For example, the administration of many of the anti-inflammatory agents is described in the "Physicians' Desk Reference" (PDR), e.g., 1996 edition (Medical Economics Company, Montvale, NJ 07645-1742, USA); the disclosure of which is incorporated herein by reference thereto.

The present invention also encompasses a pharmaceutical composition useful in the treatment of asthma and/or Th2 high molecular phenotype asthma, comprising the administration of a therapeutically effective amount of an agent that targets the Th2 inflammation pathway such as a CRTH2 inhibitor such as one or more agents of Table 2, or a combination of an agent of Table 2 together with another asthma therapy, with or without pharmaceutically acceptable carriers or diluents. The synergistic pharmaceutical compositions of this invention comprise two or more of the agents listed in Table 2 and a pharmaceutically acceptable carrier. The compositions of the present invention may further comprise one or more pharmaceutically acceptable additional ingredient(s) such as alum, stabilizers, antimicrobial agents, buffers, coloring agents, flavoring agents, adjuvants, and the like. The anti-asthma compositions of the present invention may be administered orally or parenterally including the intravenous, intramuscular, intraperitoneal, subcutaneous, aerosolized, and topical routes of administration.

Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

Certain patients can be treated effectively with a plurality of anti-asthma compounds listed in Table 2. Such combinations can provide greater efficacy. When used in such double, triple and quadruple combinations the dosages can be determined according to known protocols.

The combinations of the instant invention may also be co-administered with other well known therapeutic agents that are selected for their particular usefulness against the condition that is being treated. Combinations of the instant invention may alternatively be used sequentially with known pharmaceutically acceptable agent(s) when a multiple combination formulation is inappropriate.

Also, in general, the compounds listed do not have to be administered in the same pharmaceutical composition, and may, because of different physical and chemical characteristics, have to be administered by different routes. For example, first compound may be administered orally to generate and maintain good blood levels thereof, while a second compound may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

Numerous Chemoattractant Receptor-Homologous Molecule Expressed on Th2 Cells (CRTH2) Antagonists/inhibitors have been described. The present invention now identifies these agents as being useful in treating subjects having the SNP biomarkers of Tables 1A and 1B and the Examples. These drugs can be used alone or in combination to treat asthma in patients having the biomarkers described herein. Any of the drugs disclosed in Table 2 may be used in the methods and uses described herein.

TABLE 2

Useful agents in treating Th2-high asthma

Drug Name

ACT-453859
ACT-463036
ADC-3680
ADC-7405
ADC-9971
AM-211
AM-461
AMG-009
AP-768 (AP-761, salt form)
AP-770
ARRY-005, ARRY-006
ARRY-502
ATX-2286
ATX-2417
AZD-1981
AZD-5985
AZD-8075
BBI-5000
BI-1021958
BI-1060469
BI-671800
Thienopyrrole acetic acids, such as CRTH2 antagonists studied by Abbott
CRTH2 antagonists studied by Astellas as described below
Biaryl-type CRTh2 antagonists as studied by Almirall, as described below
Isoquinoline CRTH2 antagonists as studied by Taisho, as described below SOA-002 (mAb)
3-indolyl sultams, as studied by Athersys, as described below
7-Azaindole-3-acetic acid derivatives as studied by Novartis, as described below AM-156, AM-206
CT-133
Phenoxyacetic acid receptor antagonists of CRTH2 (DP2 receptor antagonists), as studied by Merck Serono
fevipiprant
IW-1221
KBP-7026
MK-7246
MK-1029
QAV-680
ramatroban isostere (CRTH-2 antagonists), Athersys
RG-7185
SAR-398171
Setipiprant (ACT-129968, KYTH-105)
timapiprant (OC-459, OC000459)
TM-30510
vidupiprant (AMG-853)

Additional information regarding the compounds of Table 2 is below.

ACT-453859, a 2-(1,2,3,4-tetrahydro-9H-carbazol-9-yl) acetic acid derivative, is a follow-up CRTH2 antagonist to setipiprant that is in clinical development (see Gehin M et al., *J Clin Pharmacol.* 55(7):787-97 (2015)).

ACT-463036 is a dealkylated metabolite of ACT-453859 that has also been evaluated (see Krause A et al., *Clin Pharmacokinet.* 55(7):813-21 (2016)).

ADC-3680 is a small molecule oral therapeutic CRTH2 antagonist being studied for treatment of allergic rhinitis, asthma, and chronic obstructive pulmonary disease (see Fitzgerald et al., *European Respiratory Journal* 42: P3401 (2013)).

ADC-7405 is a back-up compound of ADC-3680 that is being studied for treatment of asthma.

ADC-9971 is another back-up compound of ADC-3680 that is being studied for treatment of allergic rhinitis, asthma, and chronic obstructive pulmonary disease.

AM-211 is a small molecule oral CRTH2 antagonist being studied for treatment of asthma, chronic obstructive pulmonary disease, and respiratory disease (see Bain G et al., *J Pharmacol Exp Ther.* 338(1):290-301 (2011)). The structure of AM-211 is:

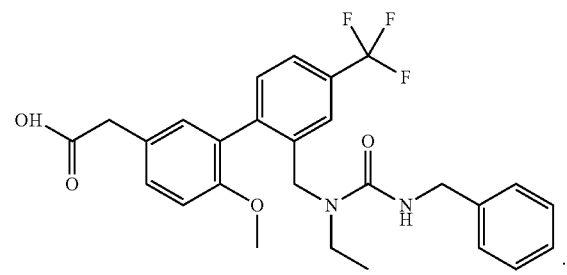 [SMILES: CCN(Cc1cc(C(F)(F)F)ccc1-c1cc(CC(=O)O)ccc1OC)C(=O)NCc1ccccc1]

AM-461 is a small molecule oral CRTH2 antagonist being studied for treatment of respiratory tract allergy (see Norman P *Expert Opin Ther Pat.* 21(12):1931-6 (2011)). The structure of AM-461 is:

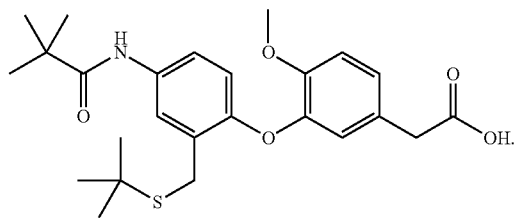 [SMILES: COc1ccc(CC(=O)O)cc1Oc1ccc(NC(=O)C(C)(C)C)cc1CSC(C)(C)C]

AMG-009 is a small molecule oral CRTH2 antagonist that can be formulated in a tablet (see Liu J et al., *Bioorg Med Chem Lett.* 19(22):6419-23 (2009)). The structure of AMG-009 is:

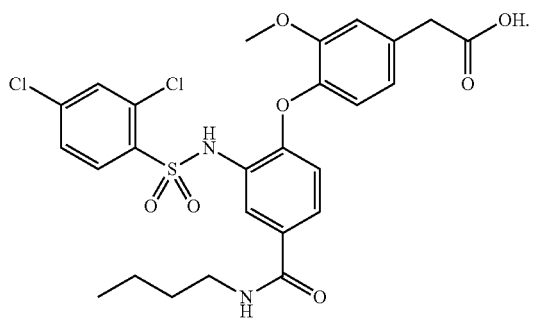 [SMILES: CCCCNC(=O)c1ccc(Oc2ccc(CC(=O)O)cc2OC)c(NS(=O)(=O)c2ccc(Cl)cc2Cl)c1]

AP-768 (AP-761, salt form) is small molecule CRTH2 antagonist described in Norman P *Expert Opinion on Investigational Drugs* 19:8 (2010). AP-770 is also a CRTH2 antagonist.

ARRY-005 and ARRY-006 are CRTH2 antagonists described in Norman P. *Expert Opin Investig Drugs.* 23(1):55-66 (2014).

ARRY-502 is a CRTH2 antagonist described in Wenzel S E et al., *J Allergy Clin Immunol* 133:2, Supplement, Page AB4 (2014) with the structure of:

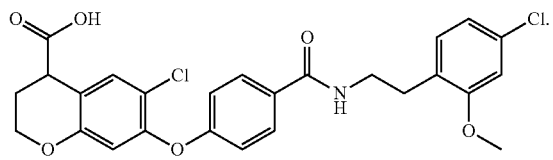 [SMILES: COc1cc(Cl)ccc1CCNC(=O)c1ccc(Oc2cc3c(cc2Cl)C(C(=O)O)CCO3)cc1]

ATX-2286 is a CRTH2 antagonist.

ATX-2417 is an oral CRTH2 antagonist that has been evaluated in clinical trial NCT02316912.

Figure 9:
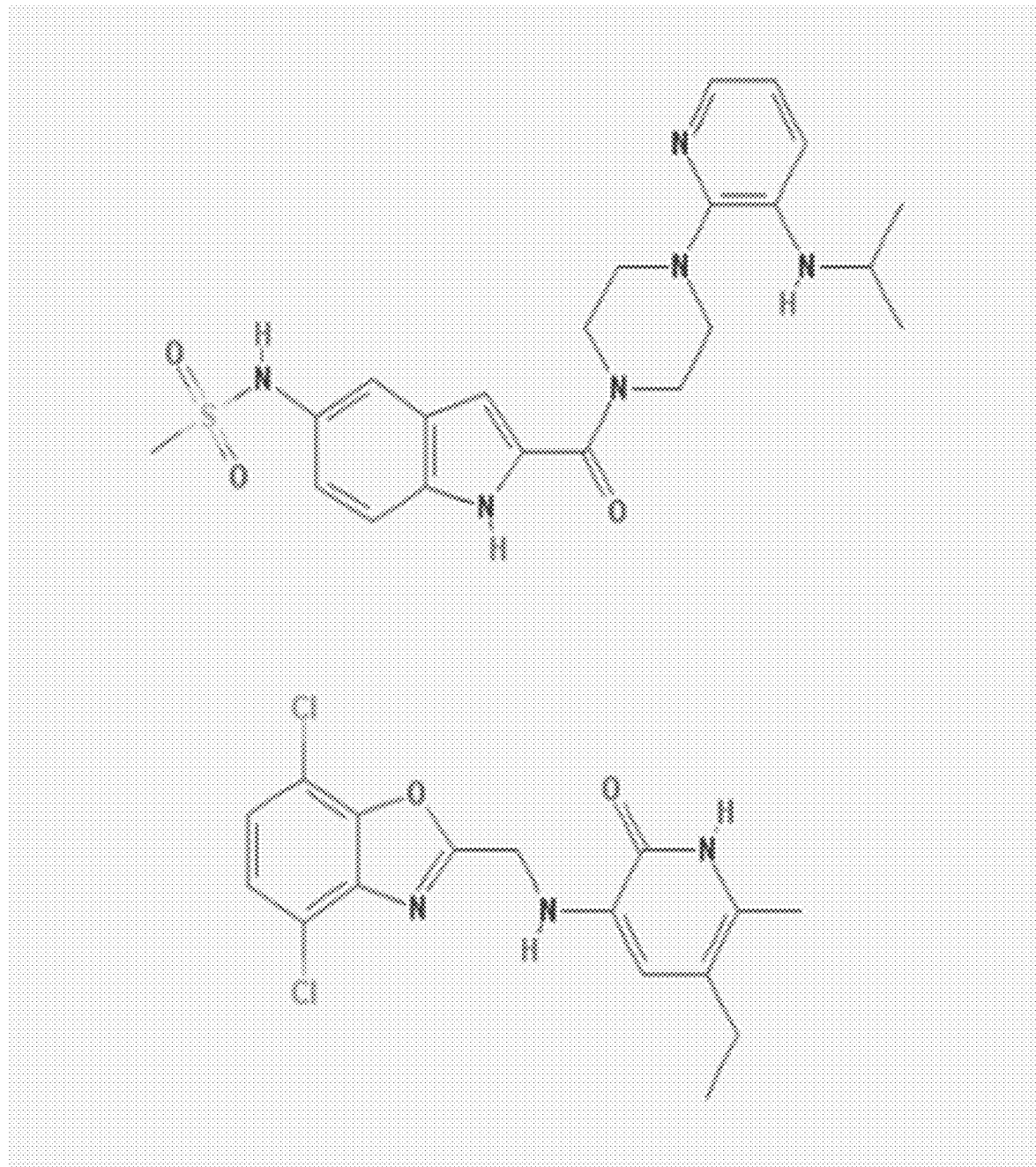
FIG. 9 provides the chemical structure of AZD-5985.

AZD-1981 is an oral CRTH2 antagonist in clinical development for asthma and chronic obstructive pulmonary disease (see Schmidt J A et al., *Br J Pharmacol.* 168(7):1626-38 (2013) and Snell N et al., *Respir Med.* 107(11):1722-30 (2013)). The structure of AZD-1981 is:

AZD-5985 is an oral CRTH2 antagonist. The pharmacokinetics of AZD-5985 have been studied in the clinical trial NCT00799331. The structure of AZD-5985 is shown in FIG. 9.

AZD-8075 is an oral CRTH2 antagonist. The pharmacokinetics of AZD-8075 have been studied in clinical trial NCT00787072.

BBI-5000 is an oral CRTH2 antagonist. The pharmacokinetics of BBI-5000 have been studied in clinical trial NCT02590289.

BI-1021958 is an oral CRTH2 antagonist that has been studied in patients with asthma in clinical trial NCT01629849.

BI 1060469 is an oral CRTH2 antagonist whose safety, pharmacokinetics, and pharmacodynamics have been evaluated in clinical trials (see Bateman E et al., *European Respiratory Journal* 48:PA4125 (2016).

BI-671800 is an oral CRTH2 antagonist that has been evaluated in patients with asthma (see Hall I P et al., *Pulm Pharmacol Ther.* 32:37-44 (2015)) and seasonal allergic rhinitis (see Krug N et al., *J Allergy Clin Immunol.* 133(2):414-9 (2014)).

The structure of BI-671800 is:

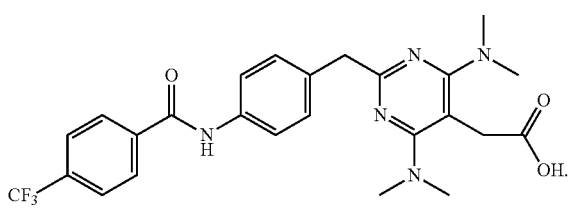 [SMILES: CN(C)c1nc(Cc2ccc(NC(=O)c3ccc(C(F)(F)F)cc3)cc2)nc(N(C)C)c1CC(=O)O]

Thienopyrrole acetic acids have been studied by Abbott and others as CRTH2 antagonists for treatment of allergic asthma, allergic rhinitis, and other inflammatory diseases (see Bonafoux D et al., *Bioorg Med Chem Lett.* 15; 21(6):1861-4 (2011)). An exemplary structure is:

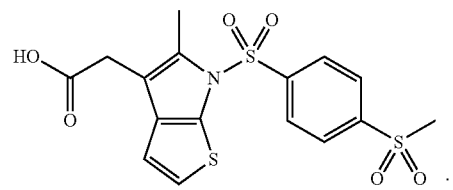 [SMILES: Cc1c(CC(=O)O)c2ccsc2n1S(=O)(=O)c1ccc(S(C)(=O)=O)cc1]

An oral CRTH2 antagonist with the structure of

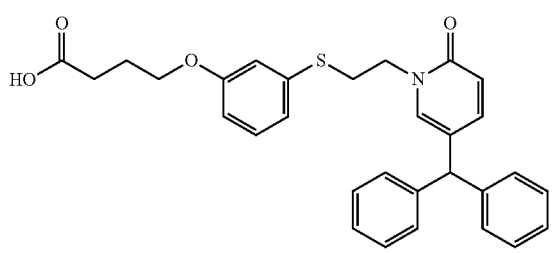 [SMILES: O=C(O)CCCOc1cccc(SCCn2cc(C(c3ccccc3)c3ccccc3)ccc2=O)c1]

has been studied by Astellas as a treatment for allergy (see Ito S et al., *Bioorg Med Chem Lett.* 22(2):1194-7 (2012)).

A biaryl series of CRTH2 antagonists have been studied by Almirall as treatments for inflammatory diseases (see Alonso J A et al., *Bioorg Med Chem Lett.* 24(21): 5127-33 (2014)). An exemplary structure is:

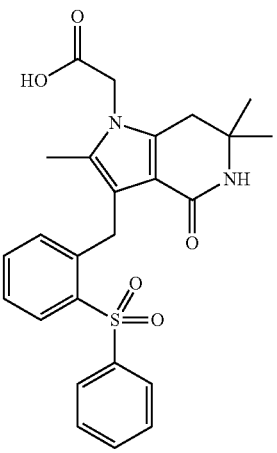

Isoquinoline CRTH2 antagonists have been investigated by Taisho as CRTH2 antagonists for treatment of asthma, allergic rhinitis, and atopic dermatitis (see Nishikawa-Shimono et al., *Chem. Pharm. Bull.* 62(6) 528-537 (2014). An exemplary structure is:

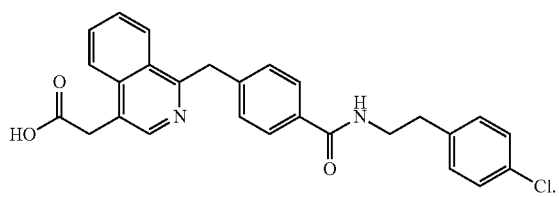 [SMILES: O=C(O)Cc1cnc(Cc2ccc(C(=O)NCCc3ccc(Cl)cc3)cc2)c2ccccc12]

SOA-002 is an anti-CRTH2 monoclonal antibody being studied for asthma, hypersensitivity, and inflammation (see adisinsight.springer.com/drugs/800018146 (2008)).

3-indolyl sultams have been studied by Athersys as selective CRTH2 antagonists (see Tumey L N et al., Bioorg Med Chem Lett. 20(11):3287-90 (2010)). A representative structure is:

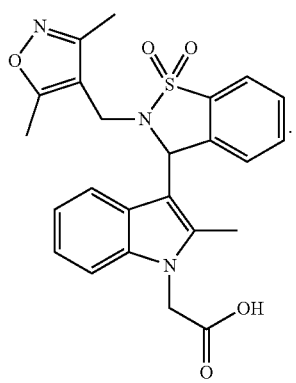 [SMILES: Cc1noc(C)c1CN1C(c2c(C)n(CC(=O)O)c3ccccc23)c2ccccc2S1(=O)=O]

7-Azaindole-3-acetic acid derivatives have been studied by Novartis as CRTH2 antagonists. A representative structure is:

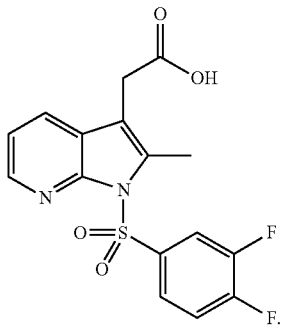 [SMILES: Cc1c(CC(=O)O)c2cccnc2n1S(=O)(=O)c1ccc(F)c(F)c1]

AM156 and AM206 are CRTH2 antagonists studied in animal models of inflammation (see Stebbins K J et al., Eur J Pharmacol. 638(1-3):142-9 (2010) and Stebbins K J et al., J Pharmacol Exp Ther. 332(3):764-75 (2010)). The structure of AM156 is:

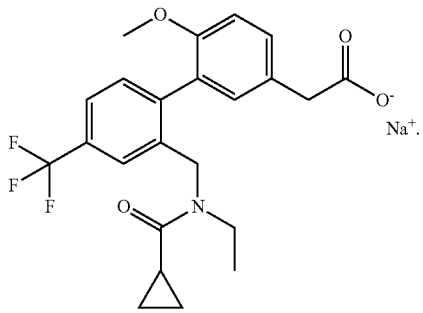 [SMILES: CCN(Cc1cc(C(F)(F)F)ccc1-c1cc(CC(=O)[O-])ccc1OC)C(=O)C1CC1]

The structure of AM206 is:

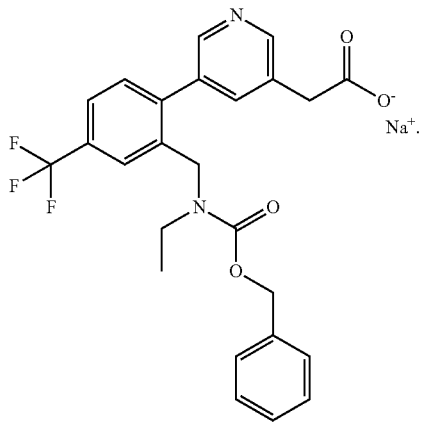

CT133 is a CRTH2 antagonist being studied by CSPC Pharmaceutical Group for treatment of allergic asthma and rhinitis (see Guo D et al., J Allergy Clin Immuno 135(2):AB3 (2015)).

Phenoxyacetic acid receptor antagonists of CRTH2 are being studied by Merck Serono (see Crosignani S et al., J. Med. Chem. 54(20):7299-7317 (2011)). A representative structure is:

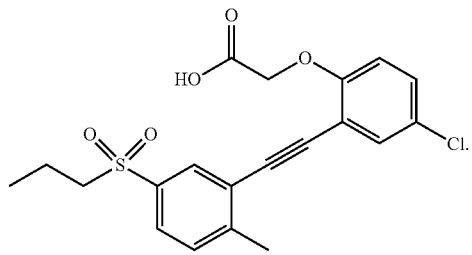 [SMILES: CCCS(=O)(=O)c1ccc(C)c(C#Cc2cc(Cl)ccc2OCC(=O)O)c1]

Fevipiprant (QAW-039) and its derivatives are being studied by as CRTH2 receptor antagonists for treatment of asthma (see Luu V T et al., J Labelled Comp Radiopharm. 58(5):188-95 (2015) and Gonem S et al., Lancet Respir Med. 4(9):699-707 (2016)). The structure of fevipiprant is:

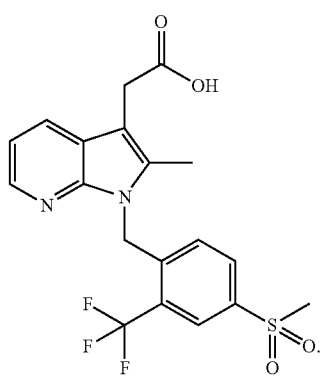 [SMILES: Cc1c(CC(=O)O)c2cccnc2n1Cc1ccc(S(C)(=O)=O)cc1C(F)(F)F]

IW-1221 is a pyrrole-based CRTH2 antagonist. Compounds in this series include 2-[3-cyano-2,5-dimethyl-4-[(2-pyrrolidin-1-ylsulfonylphenyl)methyl]pyrrol-1-yl]acetic acid.

MK-1029, an orally-available derivative of MK-7246, is a CRTH2 antagonist being studied in the NCT02720081 clinical trial of persistent asthma (see review in Norman P. *Expert Opin Investig Drugs.* 23(1):55-66 (2014)). The structure of MK-7246 (see Gattant et al *Bioorg Med Chem Lett* 21:288-293 (2011) and Gervais F G et al., *Mol Pharmacol.* 79(1):69-76 (2011)) is:

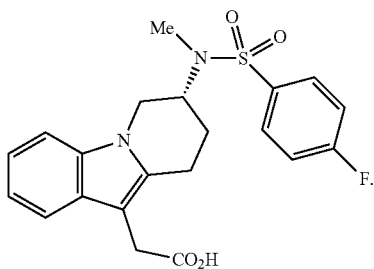 [SMILES: CN([C@@H]1CCc2c(CC(=O)O)c3ccccc3n2C1)S(=O)(=O)c1ccc(F)cc1]

KBP-7026 is a small molecule CRTH2 antagonist being evaluated for the treatment of asthma and chronic obstructive pulmonary disease.

NVP-QAV680 is an orally available CRTH2 receptor antagonist being studied in allergic disease models (see Sandham D A et al., *Bioorg Med Chem.* 21(21):6582-91 (2013) and Erpenbeck V J, *European Respiratory Journal* 44: P4075 (2014)).

The structure of NVP-QAV680 is:

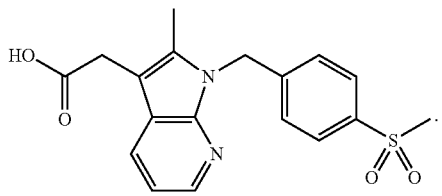 [SMILES: Cc1c(CC(=O)O)c2cccnc2n1Cc1ccc(S(C)(=O)=O)cc1]

Ramatroban isostere analogs are being studied by Athersys as CRTH2 antagonists (see Robarge M J et al., *Bioorganic & Medicinal Chemistry Letters* 15(6):1749-1753 (2005)). A representative structure is:

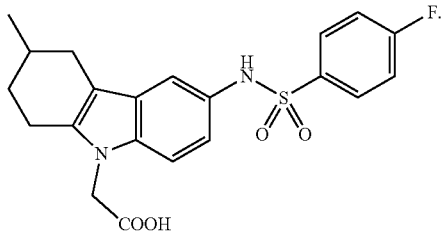 [SMILES: CC1CCc2c(c3cc(NS(=O)(=O)c4ccc(F)cc4)ccc3n2CC(=O)O)C1]

RG-7185 is a small molecule CRTH2 antagonist (see WO2010055004) with the structure:

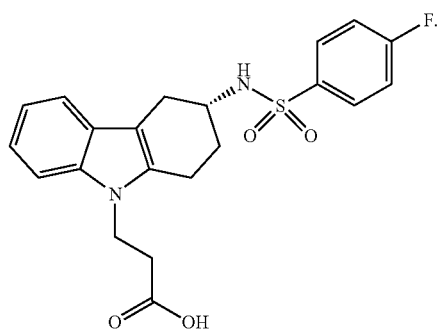 [SMILES: O=C(O)CCn1c2c(c3ccccc31)C[C@H](NS(=O)(=O)c1ccc(F)cc1)CC2]

SAR398171 is a small molecule CRTH2 antagonist.

Setipiprant (ACT-129968, KYTH-105) is an orally-available small molecule CRTH2 antagonist studied in clinical trials of pharmacokinetics (see Sidharta P N et al., *Fundam Clin Pharmacol.* 28(6):690-9 (2014)) and treatment of asthmatic males (see Diamant Z et al., *Clin Exp Allergy.* 44(8):1044-52 (2014)). The structure of setipiprant is:

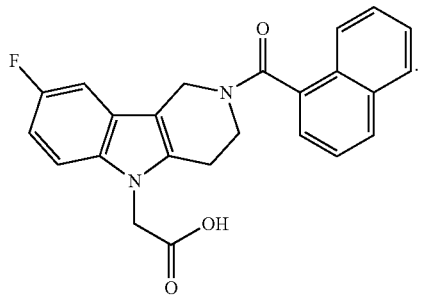 [SMILES: O=C(O)Cn1c2c(c3cc(F)ccc31)CN(C(=O)c1cccc3ccccc13)CC2]

Timapiprant (OC-459, 0C000459) is an orally-available small molecule CRTH2 that has been studied in clinical trials of asthma (see Pettipher R et al., *Allergy* 69(9): 1223-32 (2014) and Pettipher R et al., *J Pharmacol Exp Ther.* 340(2):473-82 (2012)). The structure of timapiprant is:

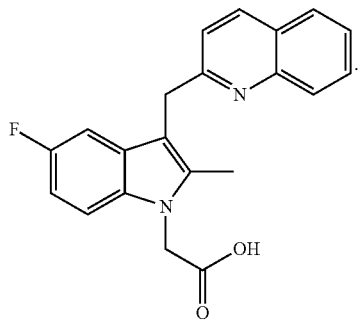 [SMILES: Cc1c(Cc2ccc3ccccc3n2)c2cc(F)ccc2n1CC(=O)O]

TM-30510 is an orally-available small molecule CRTH2 antagonist (see Grimstrup M et al., *Bioorg Med Chem Lett.* 20(5):1638-41 (2010)) with a structure of:

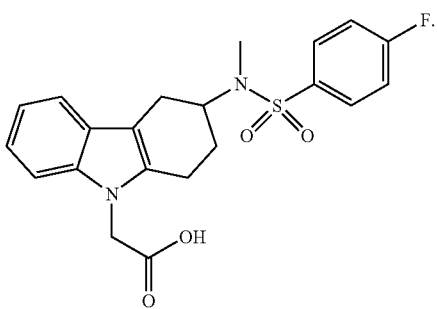 [SMILES: CN(C1CCc2c(c3ccccc3n2CC(=O)O)C1)S(=O)(=O)c1ccc(F)cc1]

Vidupiprant (AMG-853) is an orally-available small molecule CRTH2 antagonist being evaluated in clinical trials for asthma (see Liu J et al., *ACS Med Chem Lett.* 2(5):326-30 (2011) and Busse W W et al., *J Allergy Clin Immunol.* 131(2):339-45 (2013)). The structure of vidupiprant is:

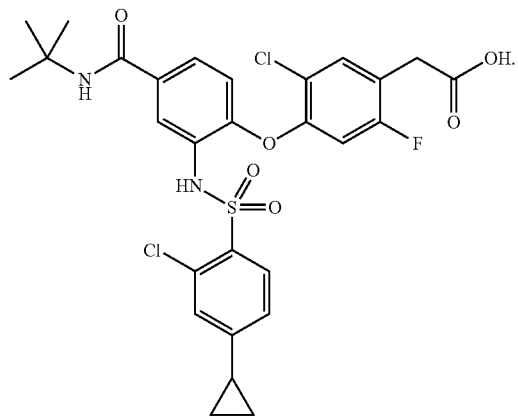 [SMILES: CC(C)(C)NC(=O)c1ccc(Oc2cc(F)c(CC(=O)O)cc2Cl)c(NS(=O)(=O)c2ccc(C3CC3)cc2Cl)c1]

In some embodiments, methods for treating asthma are encompassed comprising;
  a) obtaining a biological sample comprising nucleic acids from a human subject, or obtaining genetic information from a human subject; and
  b) detecting in said sample, or identifying in said genetic information, the presence or absence of nucleic acids harboring a combination of single nucleotide polymorphisms (SNPs) selected from 1) rs2786098 and rs2014202, 2) rs2786098 and rs7522056 or 3) rs2786098 together with any one or more of rs6673687, rs11240565, rs11240554, rs823116, rs1775146, rs1775143, rs12565321, and rs12567894; and
  c) administering an agent that targets the Th2 inflammation pathway if the combination is detected. In some embodiments, the combination of snps detected or identified is rs2786098 and rs2014202. In some embodiments, the combination of snps detected or identified is rs2786098 and rs7522056. In some embodiments, the combination of snps detected or identified is rs2786098 and rs6673687. In some embodiments, the combination of snps detected or identified is rs2786098 and rs11240565. In some embodiments, the combination of snps detected or identified is rs2786098 and rs11240554. In some embodiments, the combination of snps detected or identified is rs2786098 and rs823116. In some embodiments, the combination of snps detected or identified is rs2786098 and rs1775146. In some embodiments, the combination of snps detected or identified is rs2786098 and rs1775143. In some embodiments, the combination of snps detected or identified is rs2786098 and rs12565321. In some embodiments, the combination of snps detected or identified is rs2786098 and rs12567894. In some embodiments, the agent targets the Th2 inflammation pathway is a CRTH2 inhibitor. In some embodiments, the CRTH2 inhibitor is one or more of the agents of Table 2.

In some embodiments, methods of treating asthma are encompassed comprising administering any one or more of the agents of Table 2 to a subject having:
  1) any one or more of SNPs rs2014202, rs7522056, rs6673687, rs11240565, rs11240554, rs823116, rs1775146, rs1775143, rs12565321, and rs12567894; or
  2) rs2786098 together with any one or more of SNPs: rs2014202, rs7522056, rs6673687, rs11240565, rs11240554, rs823116, rs1775146, rs1775143, rs12565321, and rs12567894.

In some embodiments, the combination of snps detected or identified is rs2786098 and rs2014202. In some embodiments, the combination of snps detected or identified is rs2786098 and rs7522056. In some embodiments, the combination of snps detected or identified is rs2786098 and rs6673687. In some embodiments, the combination of snps detected or identified is rs2786098 and rs11240565. In some embodiments, the combination of snps detected or identified is rs2786098 and rs11240554. In some embodiments, the combination of snps detected or identified is rs2786098 and rs823116. In some embodiments, the combination of snps detected or identified is rs2786098 and rs1775146. In some embodiments, the combination of snps detected or identified is rs2786098 and rs1775143. In some embodiments, the combination of snps detected or identified is rs2786098 and rs12565321. In some embodiments, the combination of snps detected or identified is rs2786098 and rs12567894. In some embodiments, the agent is AP768 or AP770.

In some embodiments, a method of treating an asthma patient having a Th2 high molecular phenotype is provided comprising administering an agent that targets the Th2 inflammation pathway such as any one or more of the CRTH2 inhibitor agents of Table 2 to a subject having:
  1) any one or more of SNPs rs2014202, rs7522056, rs6673687, rs11240565, rs11240554, rs823116, rs1775146, rs1775143, rs12565321, and rs12567894; or
  2) rs2786098 together with any one or more of SNPs: rs2014202, rs7522056, rs6673687, rs11240565, rs11240554, rs823116, rs1775146, rs1775143, rs12565321, and rs12567894. In some embodiments, the combination of snps detected or identified is rs2786098 and rs2014202.

In some embodiments, the combination of snps detected or identified is rs2786098 and rs7522056. In some embodiments, the combination of snps detected or identified is rs2786098 and rs6673687. In some embodiments, the combination of snps detected or identified is rs2786098 and rs11240565. In some embodiments, the combination of snps detected or identified is rs2786098 and rs11240554. In some embodiments, the combination of snps detected or identified is rs2786098 and rs823116. In some embodiments, the combination of snps detected or identified is rs2786098 and rs1775146. In some embodiments, the combination of snps detected or identified is rs2786098 and rs1775143. In some embodiments, the combination of snps detected or identified is rs2786098 and rs12565321. In some embodiments, the combination of snps detected or identified is rs2786098 and rs12567894. In some embodiments, the agent is AP768 or AP770.

In some embodiments, methods of treating asthma and/or treating a Th2 high molecular phenotype asthma in a human subject is encompassed, comprising,
  a) obtaining a biological sample comprising nucleic acids from a human subject, or obtaining genetic information relating to the subject;
  b) detecting in the sample, or determining from the genetic information whether the subject has:
    i) any one or more of SNPs rs2014202, rs7522056, rs6673687, rs11240565, rs11240554, rs823116, rs1775146, rs1775143, rs12565321, and rs12567894; or
    ii) rs2786098 together with any one or more of SNPs: rs2014202, rs7522056, rs6673687, rs11240565, rs11240554, rs823116, rs1775146, rs1775143, rs12565321, and rs12567894; and
  c) administering an effective amount of an agent that targets the Th2 inflammation pathway such as any one or more of the agents of Table 2 to the subject if it is determined that the subject satisfies part i) or ii), thereby treating asthma. In some embodiments, the combination of snps detected or identified is rs2786098 and rs2014202. In some embodiments, the combination of snps detected or identified is rs2786098 and rs7522056. In some embodiments, the combination of snps detected or identified is rs2786098 and rs6673687. In some embodiments, the combination of snps detected or identified is rs2786098 and rs11240565. In some embodiments, the combination of snps detected or identified is rs2786098 and rs11240554.

In some embodiments, the combination of snps detected or identified is rs2786098 and rs823116. In some embodiments, the combination of snps detected or identified is rs2786098 and rs1775146. In some embodiments, the combination of snps detected or identified is rs2786098 and rs1775143. In some embodiments, the combination of snps detected or identified is rs2786098 and rs12565321. In some embodiments, the combination of snps detected or identified is rs2786098 and rs12567894. In some embodiments, the agent is AP768 or AP770. In some embodiments, methods of treating asthma are encompassed comprising administering an agent that targets the Th2 inflammation pathway such as one or more agent of Table 2 to a subject having a combination of snps selected from 1) rs2786098 and rs2014202, 2) rs2786098 and rs7522056, or 3) rs2786098 together with any one or more of rs6673687, rs11240565, rs11240554, rs823116, rs1775146, rs1775143, rs12565321, and rs12567894. In some embodiments, the combination of snps detected or identified is rs2786098 and rs2014202. In some embodiments, the combination of snps detected or identified is rs2786098 and rs7522056. In some embodiments, the combination of snps detected or identified is rs2786098 and rs6673687. In some embodiments, the combination of snps detected or identified is rs2786098 and rs11240565. In some embodiments, the combination of snps detected or identified is rs2786098 and rs11240554. In some embodiments, the combination of snps detected or identified is rs2786098 and rs823116. In some embodiments, the combination of snps detected or identified is rs2786098 and rs1775146. In some embodiments, the combination of snps detected or identified is rs2786098 and rs1775143. In some embodiments, the combination of snps detected or identified is rs2786098 and rs12565321. In some embodiments, the combination of snps detected or identified is rs2786098 and rs12567894. In some embodiments, the agent is AP768 or AP770.

The following examples are provided to illustrate certain embodiments of the invention. They are not intended to limit the invention in any way.

Example I

Epistatic Interaction Between DENN1B and PM20D1 Variants Defines a Subset of Th2-High Asthmatics that can be Targeted with Th2 Pathway Therapeutics We previously reported association of variants in the DENND1B gene with severe asthma (3). DENND1B has recently been shown to play a pivotal role in down-modulating surface T cell receptors (TCRs) in Th2 cells which, when dysregulated, leads to prolonged signaling, enhanced Th2 effector functions and by consequence allergic asthma (4). Crucially, that work also showed that the asthma associated variants we reported functioned similarly to engineered loss of function alleles in mice (4) indicating a direct functional role for these variants, the most significant of which is rs2786098 having the sequence of SEQ ID NO: 1 where the polymorphic site is shown in parentheses, which we published previously (3).

As a direct functional link has now been established between the variant and Th2 function, the variant genotype could be used to advantage as a proxy for Th2 status. However, to further increase discrimination, we carried out an interaction analysis of the most significant DENND1B variant rs2786098 against all other genotyped variants (epistasis) to determine if that variant interacted with any others in the genome to increase risk of developing Th2 driven asthma. Significant interaction was observed with multiple variants at a locus on chromosome 1932.1 (Table 1) the most significant of which was rs2014202 having the sequence of SEQ ID NO: 2; Interaction P-val $3.32 \times 10^{-3}$; Interaction odds ratio 1.43. These variants have not been previously reported to associate with human disease. The variants are all highly significant expression quantitative trait loci (eQTLs) for the PM20D1 gene in whole blood and further we show that they correlate very significantly (p-value $7.5 \times 10^{-27}$) with methylation patterns of PM20D1 (FIG. 1). Differential methylation of PM20D1 has been linked to asthma. Reduced methylation at the PM20D1 gene has been reported in infants born to mothers with asthma on inhaled corticosteroid treatment (5) and differential methylation of PM20D1 has also been reported in saliva and blood of individuals with respiratory allergies (6). PM20D1 encodes a secreted enzyme that has recently been reported to function in the biosynthesis of a class of N-lipidated amino acids (7). Functionally, PM20D1 remains understudied, however, as a class enzyme synthases previously associated with asthma. Th2-regulated inducible nitric oxide synthase (iNOS) enzyme has been shown to be more abundant in asthmatics and its product exhaled nitric oxide (FeNO) has been proposed as a biomarker of Th2 status (1).

TABLE 1A

Epistasis analysis interaction odds ratios (INT_OR) and interaction P values (INT_P) for the DENND1B variant (SNP1) and PM20D1 variants (SNP2), as well as the P values of the eQTL analysis of each SNP2 and the PM20D1 gene in eQTL analysis of whole blood. Ten epistatic variants demonstrated nominally significant P values of whom two (in bold) survived multiple testing correction. We note that a previously reported eQTL SNP at this locus (rs12748961) was not in LD with any of these ten SNPs and was not significant following multiple testing correction. The third column refers to the alleles in SNP2 wherein first base mentioned in the risk allele.

| SNP1 | SNP2 | chr:BP_Allele1_2 | INT_OR | INT_P | eQTL_P | eQTL effect |
|---|---|---|---|---|---|---|
| rs2786098 | rs2014202 | 1:205735612_G_A | 1.43375 | 0.00332 | 1.4E−11 | 0.46 |
| rs2786098 | rs7522056 | 1:205735891_G_A | 1.42595 | 0.003792 | 2E−11 | 0.45 |
| rs2786098 | rs6673687 | 1:205670369_A_T | 1.36646 | 0.009903 | 2.40E−10 | 0.43 |
| rs2786098 | rs11240565 | 1:205722958_C_T | 1.33684 | 0.01403 | 7.50E−15 | 0.49 |
| rs2786098 | rs11240554 | 1:205671644_C_T | 1.3718 | 0.01465 | 8.7E−12 | 0.48 |
| rs2786098 | rs823116 | 1:205720483_G_A | 1.29385 | 0.0264 | 7.40E−18 | −0.55 |
| rs2786098 | rs1775146 | 1:205756168_A_G | 1.33126 | 0.02691 | 3.1E−10 | −0.46 |
| rs2786098 | rs1775143 | 1:205755550_C_T | 1.33043 | 0.02728 | 1.3E−09 | −0.45 |
| rs2786098 | rs12565321 | 1:205755144_T_C | 1.32954 | 0.02745 | 4.8E−09 | −0.43 |
| rs2786098 | rs12567894 | 1:205755151_C_T | 1.32954 | 0.02745 | 1.2E−08 | −0.42 |

TABLE 1B

Nucleic acid sequences harboring the SNPs of the invention rs2786098  CTAAGTCAAAGGTGTTGAATTATAG[A/C]GCATTTGCCTAAAAGGAGGTTGACT (1)* rs2014202  GCTGAGGCAGGAGAATCGGTTGAAC[A/G]ATGGGAGGCGGAGGTTGCAGTGAGCT (2)

rs7522056  TAGATGAGATAGTATCCTGAGGACC[A/G]AAGAGAGACCACCTACAGAAAAAGT (3)

rs6673687  TCTTGCAGCCTTGTCCTGGGACTTC[A/T]GCCAATCTCCCCTGCCTCCCCCACT (4)

rs11240565 AAGAAATAACTTAAGACTTGAACTT[C/T]GAGTTTACTTTTTAGTGGACAAGTA (5)

rs11240554 AAAATTAGCAGCGCGTGATGGCGCA[C/T}GCCTGTAATCTCAGCTACTTGGGAG (6)

rs823116   AATGGCTAAGGCTGAGTCTGCTATC[A/G]AAAATAGACGTCAATCCCTGTCACA (7)

rs1775146  CATAGAAGGCACGCACTGGGCTAAG[A/G]AACCTGGGTGTGAATATATGACCTG (8)

rs1775143  CTTCACTTTTCTGCAATTTCTTTTT[C/T]TTTCTTGAGTTATTAAGATTTTTGT (9)

rs12565321 CACGATCTCGGTTTGCTGCAAGCTC[C/T]GCCTCCCGGGTTCACGCCATTCTCC (10)

rs12567894 TCGGTTTGCTGCAAGCTCTGCCTCC[C/T]GGGTTCACGCCATTCTCCTGCCTCA (11)

*Number in parentheses are SEQ ID NOS. The underlined base in parentheses is the risk allele.

Figure 2A:
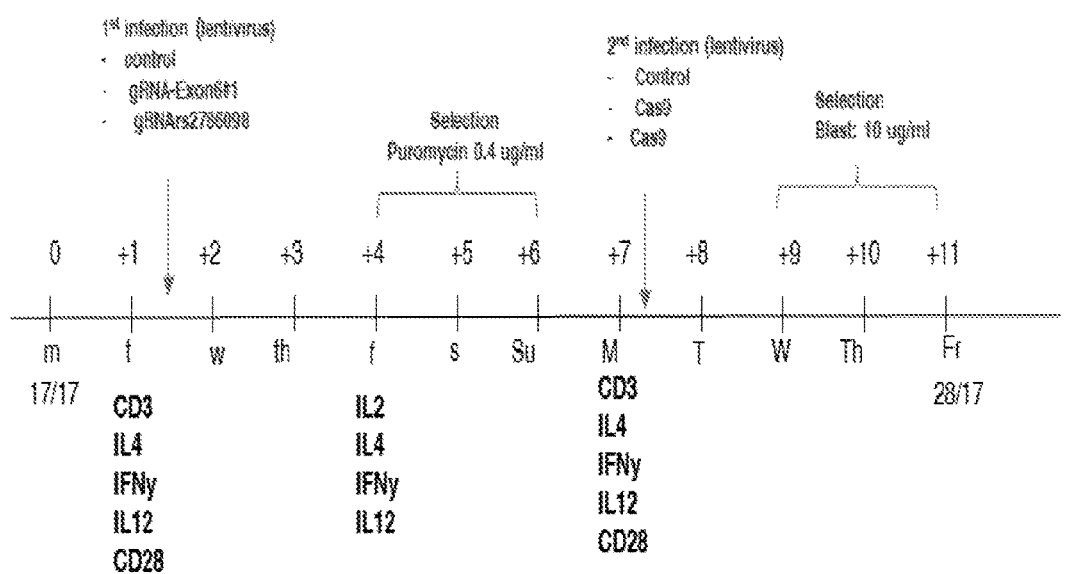
FIG. 2A demonstrates expansion and differentiation of the expanded T cells from PBMCs over 11 days.
Figure 2C:
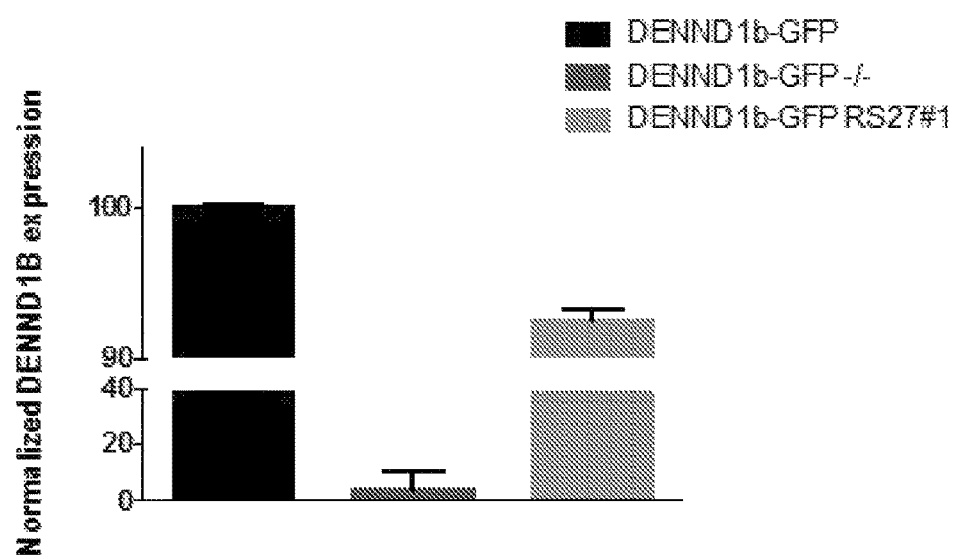
FIG. 2C shows expression of DENND1b using GFR-tag in the presence (baseline left panel) and absence (light grey panel to the right) of rs2786098 (middle panel with negative vector). Experiments were performed in triplicate and expression was consistently 12-15% lower in the absence of rs2786098, demonstrating that the SNP regulates expression of DENND1B.

Further experiments were performed to assess the lead DENND1B SNP (rs2786098) in sets of expanded T cells from healthy volunteers. FIG. 2A demonstrates expansion and differentiation of the expanded T cells from PBMCs over 11 days. FIG. 2B demonstrates excision of the lead SNP using CRISPR/Cas9. FIG. 2C shows expression of DENND1b using GFR-tag in the presence (baseline left panel) and absence (light grey panel to the right) of rs2786098 (middle panel with negative vector). Experiments were performed in triplicates and expression was consistently 12-15% lower in the absence of rs2786098, demonstrating that the SNP regulates expression of DENND1B.

FIG. 3 shows the effects on TH2 cytokine expression in the presence and absence of DENND1B knock out and after excision of the lead DENND1B SNP, rs2786098, using CRISPR. T cell differentiation was performed as previously described (FIG. 3A). Expression of IL13 and IL4 is increased following DENND1B KO and following excision of rs2786098 using CRISPR, indicating that DENND1B regulates the expression of TH2 cytokines and the expression regulation is largely attributed to the actions of rs2786098 (FIG. 3B).

As discussed above, CRTH2 is a key regulator of TH2 cytokine expression and action. We developed a CRTH2 assay to determine the effects of the SNP, rs2786098, on CRTH2 expression and action. The CRTH2 assay was developed using the following protocol. PBMCs were thawed and placed into 10 ml of RPMI+20% FBS in 15 ml conical tubes. Tubes were closed tightly, and placed on a rocker in the incubator overnight. Viable cell counts were obtained the following day. CD3+ cells were isolated from the rested PBMCs using Human T-Expander CD3/CD28 Dynabeads. These magnetic beads were used to purify CD3+/CD28+ T cells from the PBMC mixture, and then left in the cell culture to provide stimulation and co-stimulation to induce expansion of the T cells. Purified T cells were cultured with the beads in the presence of IL-2, IL-4, anti-IFNγ, and anti-IL-12. IL-2 provides a proliferative stimulus, while IL-4, anti-IFNγ, and anti-IL-12 provide TH2 skewing conditions. Cells were cultured, and culture volume was increased as required, for 10 days, at which point, they were stimulated at 500,000 cells per well with the indicated stimuli for 8 hours. Cell pellets were harvested and RNA was extracted. Gene expression was determined by qPCR.

Figure 4:
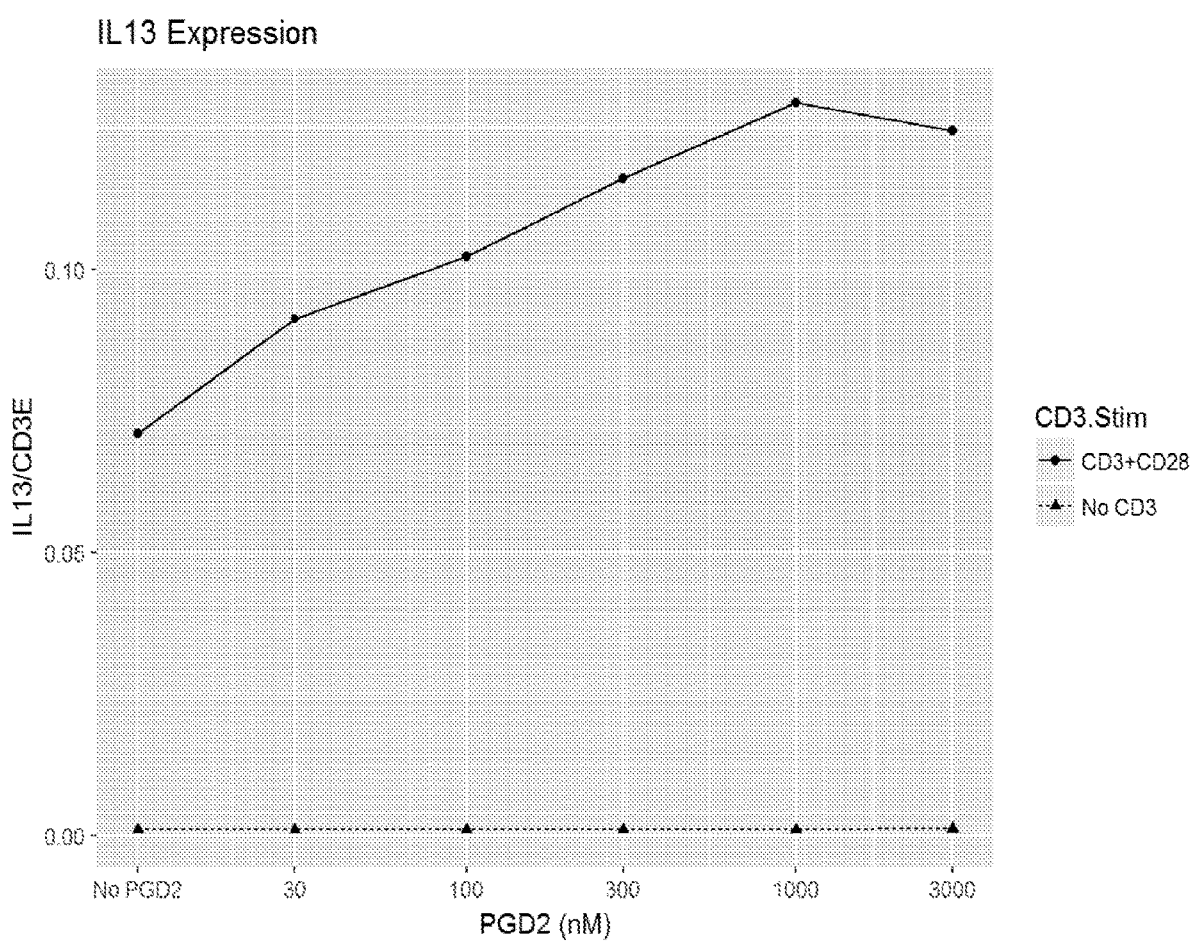
FIG. 4. T cells from a healthy human volunteers were stimulated with increasing concentrations of PGD2 (ligand for CRTH2 receptor) in the presence or absence of CD3/CD28 stimulation. CD3/CD28 stimulation was required for IL-13 production, whereas additional IL-13 was produced in the presence of PDG2.
Figure 5A:
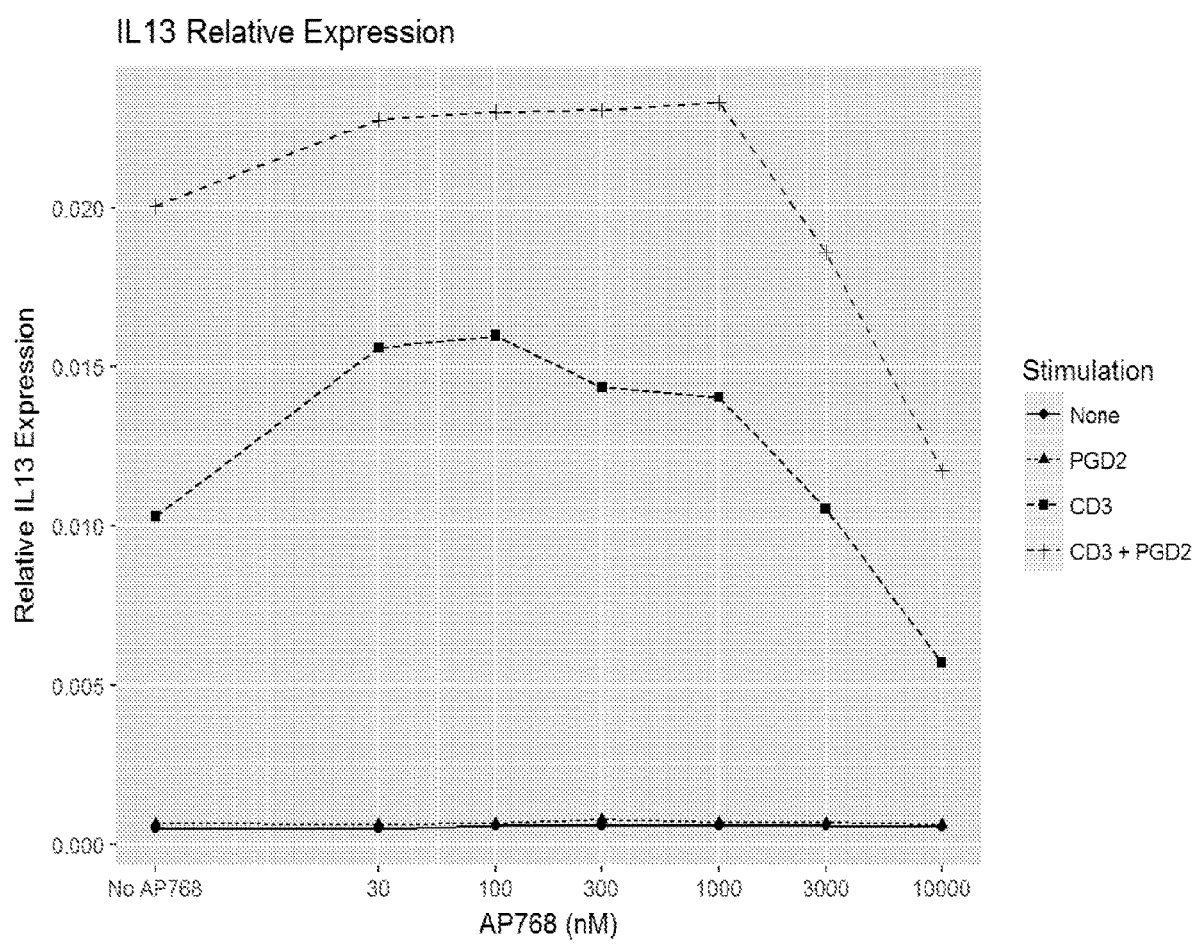

FIG. 4 is a graph showing the results after T cells from a healthy human volunteers were stimulated with increasing concentrations of PGD2 (ligand for CRTH2 receptor) in the presence or absence of CD3/CD28 stimulation. CD3/CD28 stimulation was required for IL-13 production, whereas additional IL-13 was produced in the presence of PDG2. FIG. 5A is a graph showing T cells from healthy human volunteers stimulated with 300 nM PGD2 in the presence or absence of CD3/CD28 stimulation. Stimulation occurred in the presence of increasing concentrations of the CRTH2 inhibitor AP768. Inhibition of IL-13 production was observed, indicating that the IL-13 production is mediated through the CRTH2 receptor and is inhibited at increasing concentrations of the inhibitor. FIG. 5B provides additional details of the qPCR results shown in FIGS. 4 and 5A.

Figure 6:
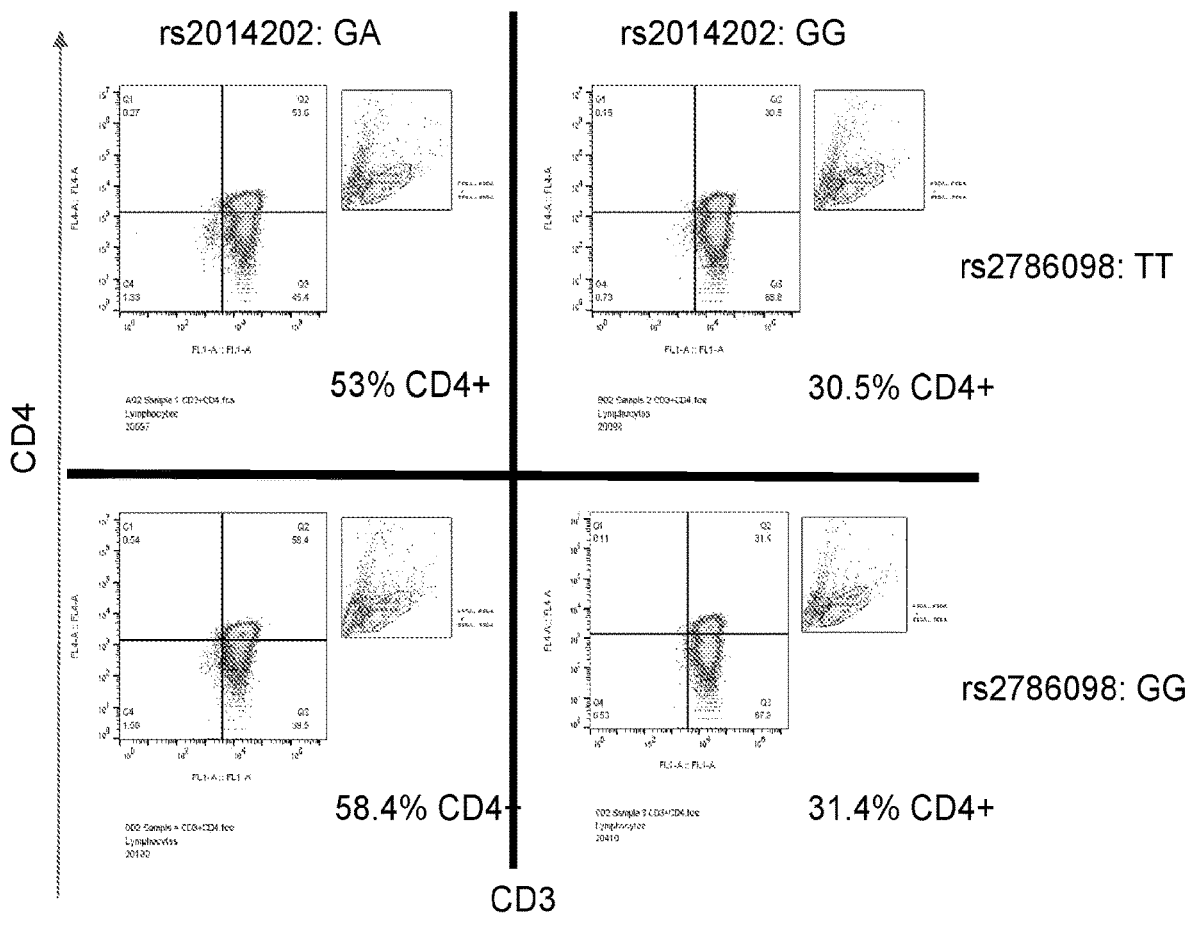
FIG. 6. After expansion for 10 days, basically all the cells are CD3+. As shown, heterozygotes at the PM20D1 SNP (risk allele A) have more CD4+ cells than homozygotes WT (GG genotype). The A allele at rs2014202 was associated in our dataset with decreased methylation at the PM20D1 locus. Decreased methylation at PM20D1 was associated with infant atopy in children born to asthmatic mothers (PMID: 24166889). Here, the A allele is associated with more CD4+ cells in the expanded T cell population. The risk allele (allele G) for the DENND1B SNP (rs2786098) enhances the CD4+ cell count further and this is more prominent in subjects with the risk allele (allele A) in the PM20D1 gene. Cells were not available for the study of the AA/GG risk genotypes.

FIG. 6 shows surface staining for CD4 on expanded T cells. After expansion for 10 days, basically all the cells are CD3+. As shown, heterozygotes at the PM20D1 SNP (risk allele A) have more CD4+ cells than homozygotes WT (GG genotype). The A allele at rs2014202 was associated in our dataset with decreased methylation at the PM20D1 locus. Decreased methylation at PM20D1 was associated with infant atopy in children born to asthmatic mothers (PMID: 24166889). Here, the A allele is associated with more CD4+ cells in the expanded T cell population. The risk allele (allele G) for the DENND1B SNP (rs2786098) enhances the CD4+ cell count further and this is more prominent in subjects with the risk allele (allele A) in the PM20D1 gene.

Figure 7:
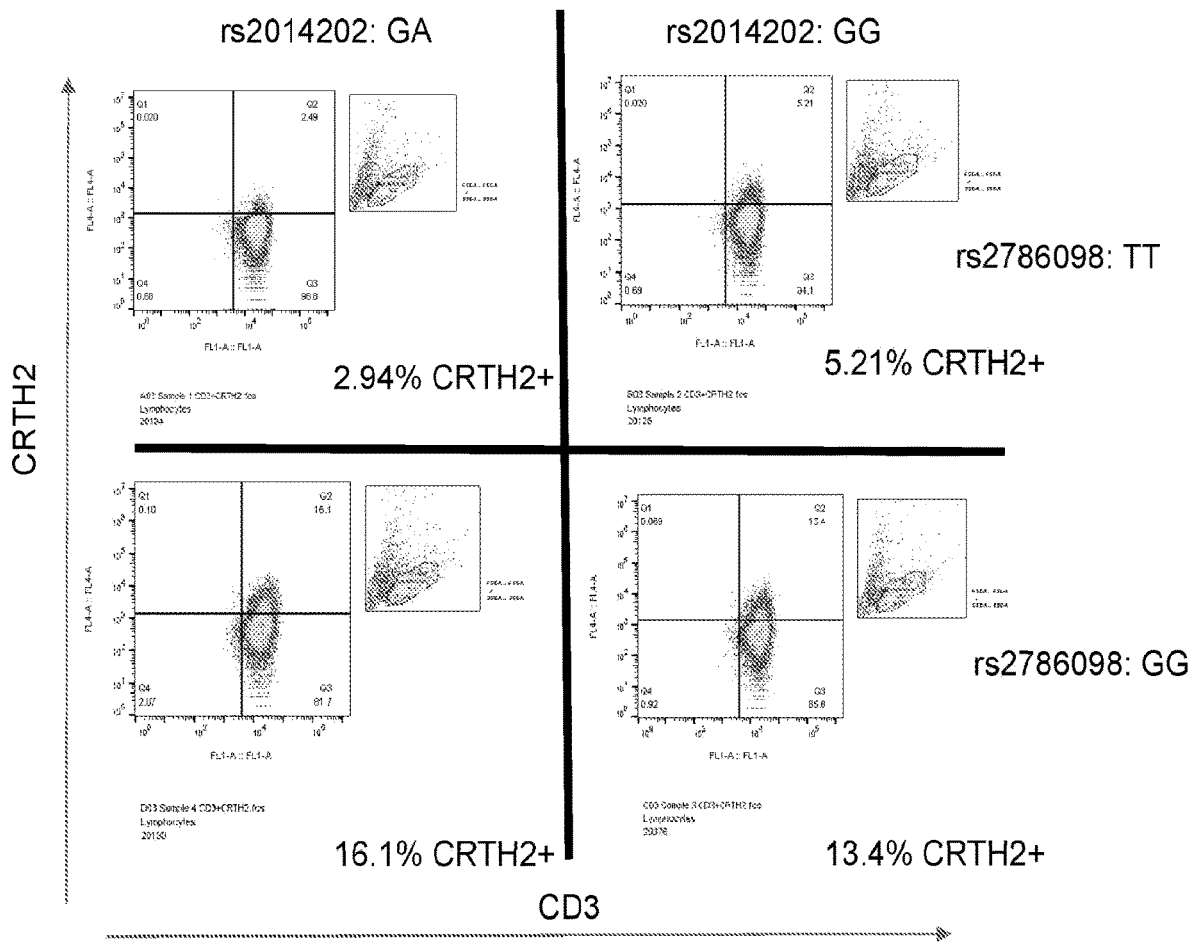
FIG. 7. CRTH2 staining was performed (CD3 on x-axis CRTH2 on y-axis) in expanded T cells from subjects with confirmed asthma diagnosis. Homozygotes for the susceptibly allele at the DENND1B SNP have more CRTH2+ cells than homozygotes for the wild type allele. Homozygotes for the susceptibly allele at the DENND1B SNP have more CRTH2+ cells than homozygotes for the resistant allele.
Figure 8A:
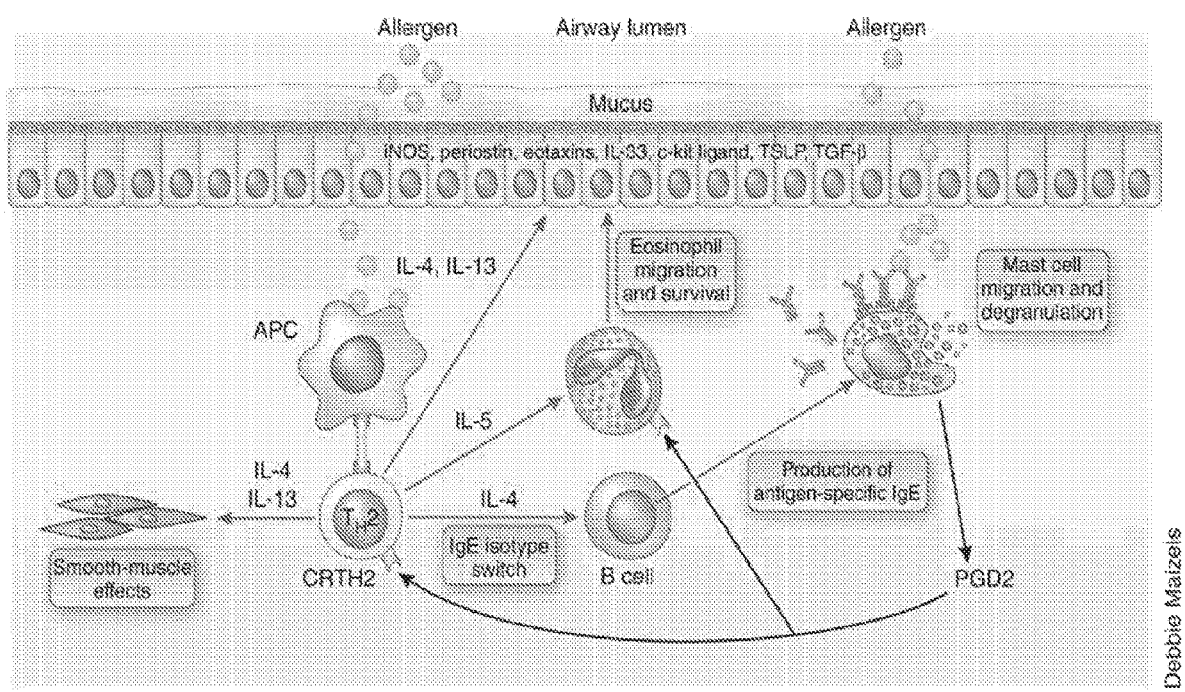
FIGS. 8A and 8B provide a schematic drawing of TH2 immune processes in the airways of people with asthma (1).
Figure 8B:
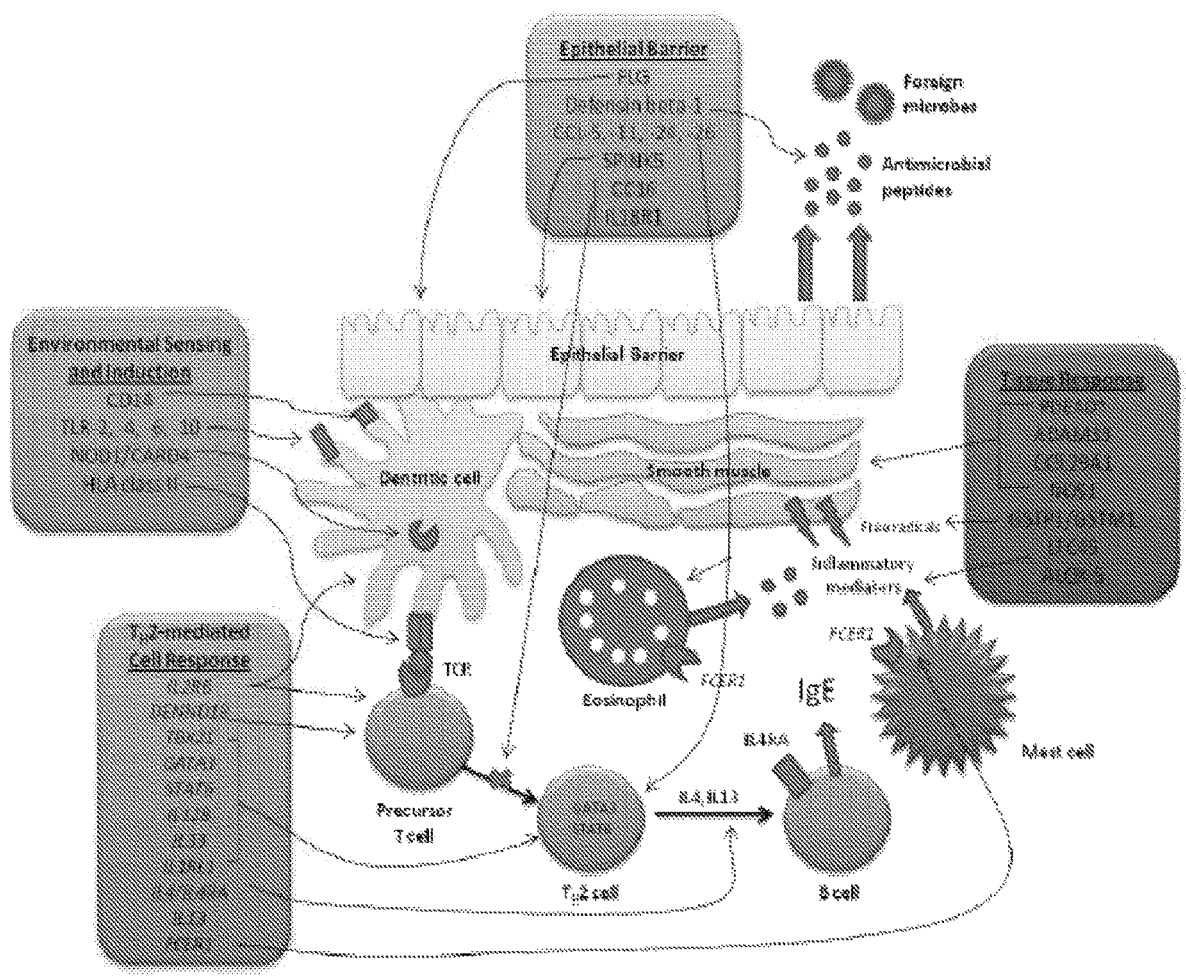

FIG. 7 shows the results of CRTH2 Staining (CD3 on x-axis CRTH2 on y-axis) in expanded T cells from subjects with confirmed asthma diagnosis. Homozygotes for the susceptibly allele at the DENND1B SNP have more CRTH2+ cells than homozygotes for the wild type allele. Homozygotes for the susceptibly allele at the DENND1B SNP have more CRTH2+ cells than homozygotes for the resistant allele.

The data above show that rs2014202 can be used alone to predict increased risk of TH2 high molecular phenotype asthma. The data also shows that rs7522056 can be used alone to predict increased risk of TH2 high molecular phenotype asthma. Further, the data show that rs2786098 and rs2014202, or rs2786098 and rs7522056 risk genotypes, which are carried by approximately 22% of the population, can be used as biomarkers in combination to genetically stratify asthma patients into a "Th2-high" stratum predicting response to novel therapeutics targeting the Th2 pathway including PGD2, PTGDR and CRTH2 as well as TSLP and DENND1B all of which have clinical relevance in treating asthma.

We also demonstrate that CRTH2 expression is higher in T cells having the DENND1B GG genotype, consistent with FACS staining. CRTH2 mRNA is downregulated after CD3 stimulation. We also show that AP768 is effective to downregulate CRTH2 via induction of CD3/CD28 down modulation. Taken together, these data demonstrate that the DENND1B/PM20D1 risk alleles described herein can be used as biomarkers for identifying subjects having T cells exhibiting enhanced CRTH2 expression and action, as indicated by the presence of elevated expression levels of TH2 cytokines and numbers of $CRTH^{2+}$ cells. The data also reveal that the CRTH2 inhibitor AP768 blocks the upregulated Th2 cytokine expression and action, and thus should have efficacy for treating asthma in subjects having these risk alleles, e.g. in patients having asthma with a Th2-high phenotype.

REFERENCES

1. Wenzel S E. Asthma phenotypes: the evolution from clinical to molecular approaches. Nat Med. 2012; 18(5): 716-25. doi: 10.1038/nm.2678. PubMed PMID: 22561835.
2. Woodruff P G, Modrek B, Choy D F, Jia G, Abbas A R, Ellwanger A, Koth L L, Arron J R, Fahy J V. T-helper type 2-driven inflammation defines major subphenotypes of asthma. Am J Respir Crit Care Med. 2009; 180(5):388-95. doi: 10.1164/rccm.200903-0392OC. PubMed PMID: 19483109; PMCID: PMC2742757.
3. Sleiman P M, Flory J, Imielinski M, Bradfield J P, Annaiah K, Willis-Owen S A, Wang K, Rafaels N M, Michel S, Bonnelykke K, Zhang H, Kim C E, Frackelton E C, Glessner J T, Hou C, Otieno F G, Santa E, Thomas K, Smith R M, Glaberson W R, Garris M, Chiavacci R M, Beaty T H, Ruczinski I, Orange J M, Allen J, Spergel J M, Grundmeier R, Mathias R A, Christie J D, von Mutius E, Cookson W O, Kabesch M, Moffatt M F, Grunstein M M, Barnes K C, Devoto M, Magnusson M, Li H, Grant S F, Bisgaard H, Hakonarson H. Variants of DENND1B associated with asthma in children. N Engl J Med. 2010; 362(1):36-44. Epub 2009/12/25. doi: NEJMoa0901867 [pii]10.1056/NEJMoa0901867. PubMed PMID: 20032318.
4. Yang C W, Hojer C D, Zhou M, Wu X, Wuster A, Lee W P, Yaspan B L, Chan A C. Regulation of T Cell Receptor Signaling by DENND1B in TH2 Cells and Allergic Disease. Cell. 2016; 164(1-2):141-55. doi: 10.1016/j.cell.2015.11.052. PubMed PMID: 26774822.
5. Gunawardhana L P, Baines K J, Mattes J, Murphy V E, Simpson J L, Gibson P G. Differential DNA methylation profiles of infants exposed to maternal asthma during pregnancy. Pediatr Pulmonol. 2014; 49(9):852-62. doi: 10.1002/ppul.22930. PubMed PMID: 24166889.
6. Langie S A, Szarc Vel Szic K, Declerck K, Traen S, Koppen G, Van Camp G, Schoeters G, Vanden Berghe W, De Boever P. Whole-Genome Saliva and Blood DNA Methylation Profiling in Individuals with a Respiratory Allergy. PLoS One. 2016; 11(3):e0151109. doi: 10.1371/journal.pone.0151109. PubMed PMID: 26999364; PMCID: PMC4801358.
7. Long J Z, Svensson K J, Bateman L A, Lin H, Kamenecka T, Lokurkar I A, Lou J, Rao R R, Chang M R, Jedrychowski M P, Paulo J A, Gygi S P, Griffin P R, Nomura D K, Spiegelman B M. The Secreted Enzyme PM20D1 Regulates Lipidated Amino Acid Uncouplers of Mitochondria. Cell. 2016; 166(2):424-35. doi: 10.1016/j.cell.2016.05.071. PubMed PMID: 27374330; PMCID: PMC4947008.
8. Romagnani S. Th1/Th2 cells Inflamm Bowel Dis. 1999 November; 5(4):285-94.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for detecting and treating asthma with a Th2 high molecular phenotype in a human asthma patient, the method comprising;
   a) obtaining a biological sample comprising nucleic acids from the human asthma patient;
   b) detecting in said sample, that the nucleic acids harbor a combination of single nucleotide polymorphisms (SNPs): a C at rs2786098 together with a G at rs2014202, said detecting of the combination indicating that said patient has asthma with a Th2 high molecular phenotype; and
   c) following said detecting, administering to the patient at least one CRTH2 inhibitor that targets the Th2 inflammation pathway selected from ACT-453859, ACT-463036, ADC-3680, ADC7405, ADC-9971, AM-211, AM-461, AMG-009, AP768, AP 770, AP761, ARRY-005, ARRY-006, ARRY-502, ATX-2286, ATX-2417, AZD-1981, AZD-5985, AZD-9075, BBI-5000, BI-1021958, BI 1060469, BI-671800, thienopyrrole acetic acids, isoquinoline CRTH1 antagonist, SOA-002, 3-indolyl sultams, AM156, AM206, CT133, fevipiprant, IW-1221, MK-1029, KBP-7026, NVP-QAV680, RG-7185, SAR398171, setipiprant, timapiprant, TM-30510, and vidupiprant
   wherein said SNPs in said combination are detected by performing a process selected from detection of specific hybridization, measurement of allele size, restriction fragment length polymorphism analysis, allele-specific hybridization analysis, single base primer extension reaction, and sequencing of an amplified polynucleotide.

2. The method of claim 1, further comprising detecting in said sample that the nucleic acids harbor one or more single nucleotide polymorphism (SNP) having rs numbers selected from a G at rs7522056, an A at rs6673687, a C at rs11240565, a C at rs11240554, a G at rs823116, an A at rs1775146, a C at rs1775143, a T at rs12565321, and a C at rs12567894.

3. The method as claimed in claim 1, wherein the nucleic acids are amplified prior to detection of the SNPs in the combination.

4. The method of claim 1, wherein the nucleic acids are obtained from isolated cells from the human patient.

5. A method for treating asthma comprising;
   a) obtaining a biological sample comprising nucleic acids from a human patient, or obtaining genetic information from a human patient;
   b) detecting in the sample, or determining from the genetic information, that a combination of single nucleotide polymorphisms (SNPs), a C at rs2786098 together with a G at rs2014202, is present in said human patient; and
   c) following step (b), administering to said human patient an agent that targets the Th2 inflammation pathway.

6. The method of claim 5, further comprising detecting in said sample that the nucleic acids harbor one or more single nucleotide polymorphism (SNP) having rs numbers selected from a G at rs7522056, an A at rs6673687, a C at rs11240565, a C at rs11240554, a G at rs823116, an A at rs1775146, a C at rs1775143, a T at rs12565321, and a C at rs12567894.

7. The method of claim 6, wherein said agent is selected from CRTH2 inhibitors ACT-453859, ACT-463036, ADC-3680, ADC7405, ADC-9971, AM-211, AM-461, AMG-009, AP768, AP 770, AP761, ARRY-005, ARRY-006, ARRY-502, ATX-2286, ATX-2417, AZD-1981, AZD-5985, AZD-9075, BBI-5000, BI-1021958, BI 1060469, BI-671800, thienopyrrole acetic acids, isoquinoline CRTH1 antagonist, SOA-002, 3-indolyl sultams, AM156, AM206, CT133, fevipiprant, IW-1221, MK-1029, KBP-7026, NVP-QAV680, RG-7185, SAR398171, setipiprant, timapiprant, TM-30510, and vidupiprant.

8. A method for treating Th2 high molecular phenotype asthma in a human patient, comprising,
   a) obtaining a biological sample comprising nucleic acids from a human subject, or obtaining genetic information relating to the human patient;
   b) detecting in the sample, or determining from the genetic information, that the human patient has: a C at rs2786098 together with a G at rs2014202; and
   c) following b), administering an effective amount of one or more agents that target the Th2 inflammation pathway thereby treating Th2-high asthma wherein said one or more agents is selected from ACT-453859, ACT-463036, ADC-3680, ADC7405, ADC-9971, AM-211, AM-461, AMG-009, AP768, AP 770, AP761, ARRY-005, ARRY-006, ARRY-502, ATX-2286, ATX-2417, AZD-1981, AZD-5985, AZD-9075, BBI-5000, BI-1021958, BI 1060469, BI-671800, thienopyrrole acetic acids, isoquinoline CRTH1 antagonist, SOA-002, 3-indolyl sultams, AM156, AM206, CT133, feviprant, IW-1221, MK-1029, KBP-7026, NVP-QAV680, RG-7185, SAR398171, setipiprant, timapiprant, TM-30510, and vidupiprant.

9. The method of claim 8, wherein said one or more agents includes AP768 or AP770.

10. The method of claim 8, further comprising detecting in said sample that the nucleic acids harbor one or more single nucleotide polymorphism (SNP) having rs numbers selected from a G at rs7522056, an A at rs6673687, a C at rs11240565, a C at rs11240554, a G at rs823116, an A at rs1775146, a C at rs1775143, a T at rs12565321, and a C at rs12567894.

* * * * *

SEQUENCE LISTING

<160> NUMBER OF SEQ ID NOS: 11

<210> SEQ ID NO 1
<211> LENGTH: 51
<212> TYPE: DNA
<213> ORGANISM: Homo sapiens

<400> SEQUENCE: 1
ctaagtcaaa ggtgttgaat tatagmgcat ttgcctaaaa ggaggttgac t        51

<210> SEQ ID NO 2
<211> LENGTH: 51
<212> TYPE: DNA
<213> ORGANISM: Homo sapiens

<400> SEQUENCE: 2
gctgaggcag gagaatcggt tgaacrtggg aggcggaggt tgcagtgagc t        51

<210> SEQ ID NO 3
<211> LENGTH: 51
<212> TYPE: DNA
<213> ORGANISM: Homo sapiens

<400> SEQUENCE: 3
tagatgagat agtatcctga ggaccraaga gagaccacct acagaaaaag t        51

<210> SEQ ID NO 4
<211> LENGTH: 51
<212> TYPE: DNA
<213> ORGANISM: Homo sapiens

<400> SEQUENCE: 4
tcttgcagcc ttgtcctggg acttcwgcca atctcccctg cctcccccac t        51

<210> SEQ ID NO 5
<211> LENGTH: 51
<212> TYPE: DNA
<213> ORGANISM: Homo sapiens

<400> SEQUENCE: 5
aagaaataac ttaagacttg aacttygagt ttacttttta gtggacaagt a        51

<210> SEQ ID NO 6
<211> LENGTH: 50
<212> TYPE: DNA
<213> ORGANISM: Homo sapiens

<400> SEQUENCE: 6
aaaattagca gcgcgtgatg gcgcayccctg taatctcagc tacttgggag         50

<210> SEQ ID NO 7
<211> LENGTH: 50
<212> TYPE: DNA
<213> ORGANISM: Homo sapiens

<400> SEQUENCE: 7
aatggctaag gctgagtctg ctatcraaat agacgtcaat ccctgtcaca         50

<210> SEQ ID NO 8
<211> LENGTH: 50
<212> TYPE: DNA
<213> ORGANISM: Homo sapiens

<400> SEQUENCE: 8

```
catagaaggc acgcactggg ctaagracct gggtgtgaat atatgacctg        50

<210> SEQ ID NO 9
<211> LENGTH: 50
<212> TYPE: DNA
<213> ORGANISM: Homo sapiens

<400> SEQUENCE: 9
cttcactttt ctgcaatttc tttttyttct tgagttatta agattttgt         50

<210> SEQ ID NO 10
<211> LENGTH: 50
<212> TYPE: DNA
<213> ORGANISM: Homo sapiens

<400> SEQUENCE: 10
cacgatctcg gtttgctgca agctcycctc ccgggttcac gccattctcc        50

<210> SEQ ID NO 11
<211> LENGTH: 50
<212> TYPE: DNA
<213> ORGANISM: Homo sapiens

<400> SEQUENCE: 11
tcggtttgct gcaagctctg cctccyggtt cacgccattc tcctgcctca        50
```